United States Patent [19]

Bessler et al.

[11] Patent Number: 5,411,508
[45] Date of Patent: May 2, 1995

[54] GASTROINTESTINAL APPROXIMATING AND TISSUE ATTACHING DEVICE

[75] Inventors: Marc Bessler, Teaneck, N.J.; Michael R. Treat, New York, N.Y.

[73] Assignee: The Trustees of Columbia University in the City of New York, New York, N.Y.

[21] Appl. No.: 39,913

[22] Filed: Mar. 30, 1993

Related U.S. Application Data

[63] Continuation-in-part of Ser. No. 783,909, Oct. 29, 1991, Pat. No. 5,197,649.

[51] Int. Cl.⁶ .............................................. A61B 17/04
[52] U.S. Cl. ......................................... 606/153; 128/4; 227/179; 227/19
[58] Field of Search .................. 128/4; 227/178–181, 227/156, 19; 606/153

[56] References Cited

U.S. PATENT DOCUMENTS

| | | |
|---|---|---|
| 3,193,165 | 8/1962 | Akhalaya et al. . |
| 3,256,875 | 5/1963 | Tsepelev et al. . |
| 3,388,847 | 6/1968 | Kasulin et al. . |
| 3,552,626 | 1/1971 | Astafiev et al. . |
| 3,858,577 | 1/1975 | Basset et al. . |
| 3,859,986 | 1/1975 | Okada et al. . |
| 4,085,756 | 4/1978 | Weaver . |
| 4,198,960 | 4/1980 | Utsugi . |
| 4,198,982 | 4/1980 | Fortner et al. . |
| 4,202,479 | 5/1980 | Razgulov et al. . |
| 4,207,898 | 6/1980 | Becht . |
| 4,250,873 | 2/1981 | Bonnet . |
| 4,273,109 | 6/1981 | Enderby . |
| 4,273,111 | 6/1981 | Tsukaya . |
| 4,286,585 | 9/1981 | Ogawa . |
| 4,289,133 | 9/1981 | Rothfuss . |
| 4,304,236 | 12/1981 | Conta et al. . |
| 4,310,115 | 1/1982 | Inoue . |
| 4,319,576 | 3/1982 | Rothfuss . |
| 4,351,146 | 9/1982 | Faure et al. ............................ 57/6 |
| 4,351,466 | 9/1982 | Noiles . |
| 4,414,800 | 11/1983 | Nakayama et al. ................ 57/236 |
| 4,445,892 | 5/1984 | Hussein et al. . |
| 4,448,188 | 5/1984 | Loeb . |
| 4,473,077 | 9/1984 | Noiles et al. . |
| 4,476,863 | 10/1984 | Kanshin et al. . |
| 4,485,817 | 12/1984 | Swiggett . |
| 4,488,523 | 12/1984 | Schichman . |

(List continued on next page.)

FOREIGN PATENT DOCUMENTS 3300768 4/1985 Germany .
7711347 10/1987 Netherlands .

*Primary Examiner*—Stephen C. Pellegrino
*Assistant Examiner*—Gary Jackson
*Attorney, Agent, or Firm*—John P. White; Peter J. Phillips

[57] ABSTRACT

An intestinal steerable endoscopic stapler for stapling tubular tissue is provided comprising a circular anvil member having a circular anvil stapling surface and a cutting block surface radially inwardly of the stapling surface. A head assembly has a circular staple driver for driving staples in an array corresponding to the anvil surface and a circular cutting blade corresponding to the cutting block. A flexible tube has a distal end at the head assembly and a handpiece end. A scope in the form of an eyepiece in the handpiece optically connected to a lens in the head assembly is provided for viewing a region of space beyond the head assembly. A steering arrangement is provided for pivoting the head assembly relative the flexible tube to thereby steer the head assembly in a body cavity. A stapler activator is provided located at the handpiece end for driving staples from the head assembly toward the anvil member and for driving the cutting blade toward the cutting block, whereby two ends of tubular tissue may be joined by an array of staples and excess tubular tissue ends may be trimmed off with the cutting blade. A number of tissue approximating devices are also disclosed.

38 Claims, 15 Drawing Sheets

U.S. PATENT DOCUMENTS

| | | |
|---|---|---|
| 4,499,895 | 2/1985 | Takayama . |
| 4,505,272 | 3/1985 | Utyamyshev et al. . |
| 4,505,414 | 3/1985 | Filipi . |
| 4,574,806 | 3/1986 | McCarthy . |
| 4,576,167 | 3/1986 | Noiles . |
| 4,589,412 | 5/1986 | Kensey . |
| 4,592,354 | 6/1986 | Rothfuss . |
| 4,593,679 | 6/1986 | Collins . |
| 4,603,693 | 8/1986 | Conta et al. . |
| 4,606,343 | 8/1986 | Conta et al. . |
| 4,610,383 | 9/1986 | Rothfuss et al. . |
| 4,646,745 | 3/1987 | Noiles . |
| 4,667,673 | 5/1987 | Li . |
| 4,671,445 | 6/1987 | Barker et al. . |
| 4,672,961 | 6/1987 | Davies . |
| 4,696,667 | 9/1987 | Nasch . |
| 4,700,703 | 10/1987 | Resnick et al. . |
| 4,703,887 | 11/1987 | Clanton et al. . |
| 4,708,141 | 11/1987 | Inoue et al. . |
| 4,752,024 | 1/1988 | Green et al. . |
| 4,754,909 | 7/1988 | Barker et al. . |
| 4,756,309 | 7/1988 | Sachse et al. . |
| 4,760,840 | 8/1988 | Fournier, Jr. et al. . |
| 4,776,506 | 10/1968 | Green . |
| 4,817,847 | 4/1989 | Redtenbacher et al. . |
| 4,819,632 | 4/1989 | Davies . |
| 4,873,977 | 10/1989 | Avant et al. . |
| 4,893,622 | 1/1990 | Green et al. . |
| 4,903,697 | 2/1990 | Resnick et al. . |
| 4,907,591 | 3/1990 | Vasconcellos et al. . |
| 4,917,114 | 4/1990 | Green et al. . |
| 4,957,499 | 9/1990 | Lipator et al. . |
| 4,962,877 | 10/1990 | Hervas . |
| 4,974,408 | 12/1990 | Karhu ................................ 57/293 |
| 4,976,710 | 12/1990 | Mackin . |
| 4,994,060 | 2/1991 | Rink et al. . |
| 5,015,249 | 5/1991 | Nakao et al. . |
| 5,037,433 | 8/1991 | Wilk et al. . |
| 5,047,039 | 9/1991 | Avant et al. . |

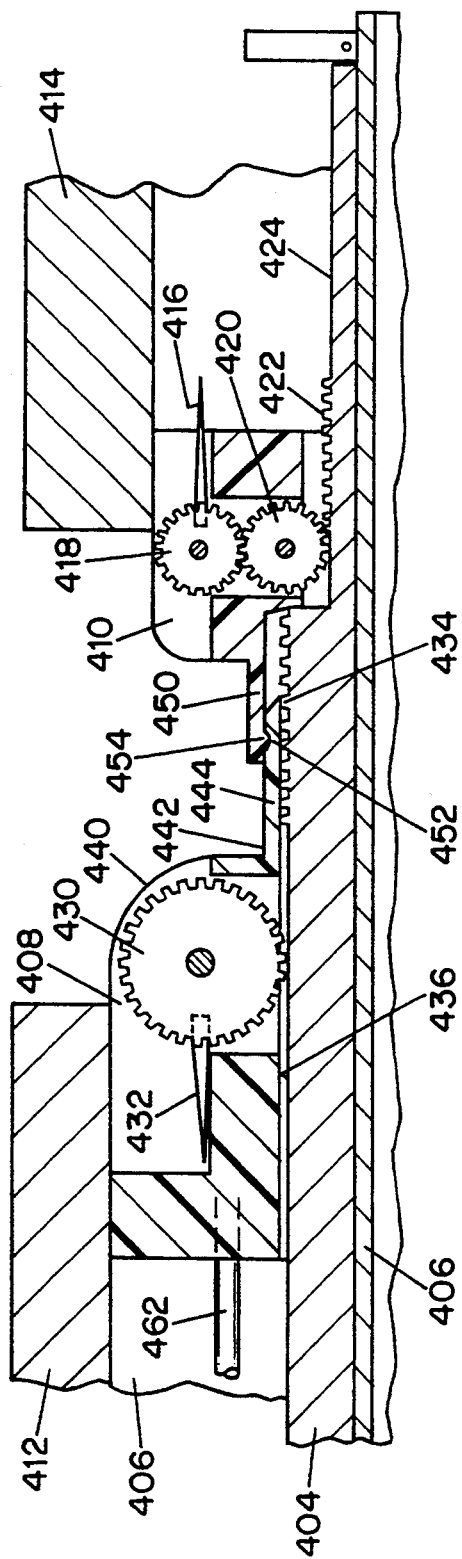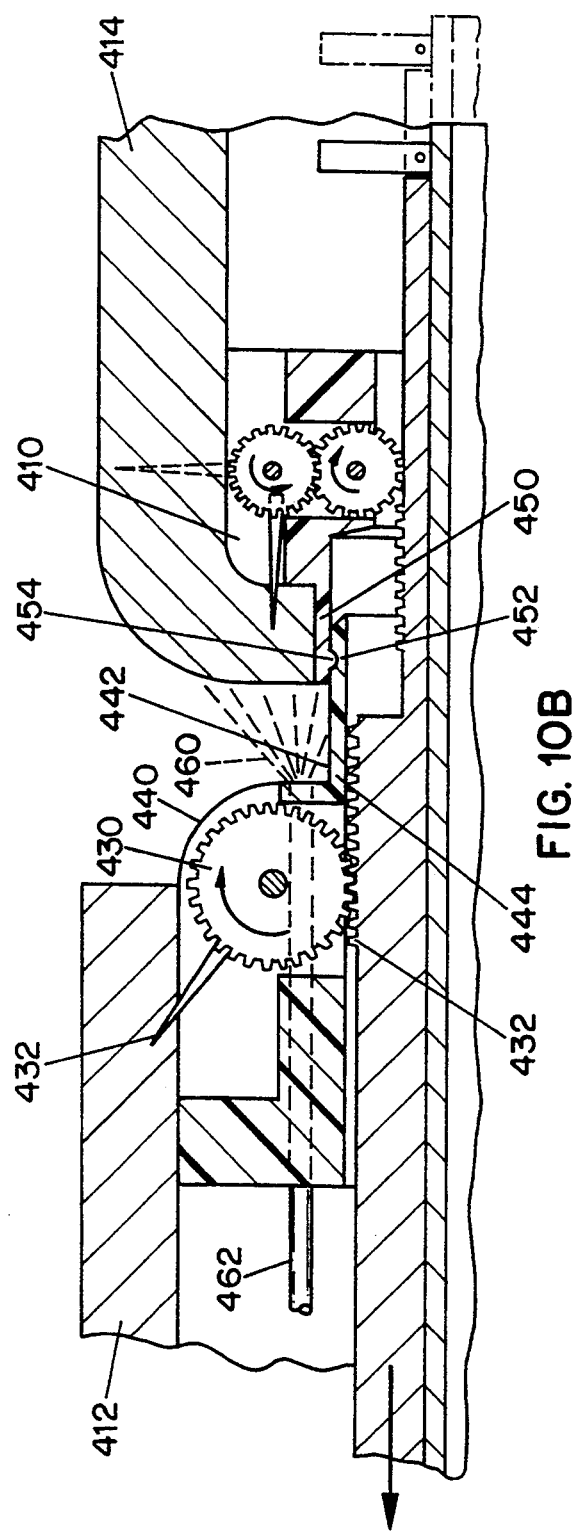

GASTROINTESTINAL APPROXIMATING AND TISSUE ATTACHING DEVICE

CROSS-REFERENCE TO RELATED APPLICATIONS

This application is a continuation-in-part of U.S. Ser. No. 07/783,909, filed Oct. 29, 1991 now U.S. Pat. No. 5,199,649.

BACKGROUND OF THE INVENTION

This invention relates to surgical gastrointestinal approximating devices and more particularly to a surgical approximating and attaching device for effecting closure of circular anastomosis.

A colon resection operation involves removing a section of the tubular colon which has become diseased and then joining the ends in an end-to-end anastomosis ("EEA"). Approximately 100,000 colon resections are performed each year in the United States, 70% of which are distal to the right colon. Although gastrointestinal anastomosis ("GIA") stapling devices are available for some colon resections, most surgeons do not use such devices to create left sided colonic anastomosis, and only about 15% of colon anastomosis are within reach of the existing EEA devices through the rectum.

Various types of circular anastomosis stapler devices are available for effecting end-to-end circular anastomosis stapling. Examples of such devices are described in U.S. Pat. No. 4,752,024, U.S. Pat. No. 4,485,817 and patents cited therein. Such stapling devices typically comprise a fastener holding assembly and an anvil assembly located at the distal end of a stapling mechanism, with means to control the spacing distance between the anvil assembly and fastener holding assembly. During surgical operations, when a surgeon desires to join by stapling two ends of tubular tissue, such as a colon in a colon resection operation, the device is inserted through the colon so that the cut between the two colon sections is disposed in a space between the anvil and stapling mechanism. Purse string-like sutures are made in both colon ends with the sutures pulled tight. A mechanism then pulls the anvil and the stapling mechanism together whereby one or more staples effect an annular stapling function, and a circular cutting blade disposed radially inwardly of the annular stapling array cuts out the remaining tissue radially inwardly of the annular staple ring. The apparatus is then removed from the colon, leaving a clean cut line and an annular array of staples holding the two previously unjoined colon portions together.

While the above-described devices have been effective for making end-to-end anastomosis, many of these devices suffer from disadvantages. Many of these devices do not have any effective means for approximating the tissue ends prior to effecting an anastomosis function, such as by stapling or other attachment means.

Many of the available devices have a rigid structure which preclude their application for other than straight intestines. Some of these devices additionally suffer from a disadvantage in that anastomosis may be effected only for a limited distance from the entrance cavity, such as the rectum. While some of these devices have employed flexible structure such as a flexible sheath or tube to enable their application to curved intestines, such devices do not provide means for steering the device through a curved section of an intestine, or to branch the device to a selected one of two or more branches in an intestine. Further, these devices also fail to provide means for viewing the surgical site or an interior human cavity on route to the surgical site.

SUMMARY OF THE INVENTION

It is an object of the present invention to provide a tissue approximating device for approximating ends of tubular tissue for anastomosis procedures, such as stapling or other attachment means.

It is another object of the present invention to provide a surgical stapler apparatus which is flexible to enable its application for curved intestines or the like.

It is an object of the present invention to provide a device which effects creation of a stapled end-to-end, end-to-side or side-to-side anastomosis virtually anywhere in the gastrointestinal tract.

It is another object of the present invention to provide a stapling device having a steering capability to steer the head of the device to a desired location along curved intestines or other surfaces or passageways in a surgical subject.

It is another object of the present invention to provide a surgical stapling device having means for viewing the surgical site as well as for viewing the travel of the device on route to the surgical site.

It is another object of the present invention to provide a surgical stapling device having means for viewing the surgical site from inside the intestine before, during and after stapling.

It is another object of the present invention to provide surgical tissue approximating device for approximating and holding tissue for tissue attaching operations such as stapling, clamping, suturing, stenting, lasing, gluing and/or heating, for example.

According to one aspect of the invention, an endoscopic surgical anastomotic device is provided, comprising: anastomotic approximating assembly for approximating two ends of anastomotic tissue, which includes, a first member which defines a tissue engaging surface; and a second member defining a tissue contacting, surface which is adapted to align with said tissue engaging surface; moving means associated with said anastomotic approximating assembly for moving said first member and said second member relative to one another between a first, spaced position in which said tissue engaging surface is spaced from said tissue contacting surface for receiving tissue therebetween, and a second approximated position in which said tissue engaging surface and said tissue contacting surface are in close cooperative alignment; imaging means associated with one of said first member and said second member for obtaining an image of an interior body region; an elongated member having a proximal and distal end, said anastomotic approximating assembly being positioned at and cooperating with said distal end of said elongated member; and a handpiece positioned at and cooperating with said proximal end of said elongated member, said handpiece including first control means operatively connected through said elongated member with said moving means for causing said first member and said second member to move between said first and second positions; and viewing means operatively connected through said elongated member with said imaging means for viewing said interior body region image.

According to another aspect of the invention, a steerable surgical anastomotic device is provided, comprising: anastomotic approximating assembly for approximating two ends of anastomotic tissue, for attaching operations which includes: a first member which defines a tissue engaging surface; and a second member defining a tissue contacting surface which is adapted to align with said tissue engaging surface; moving means associated with said anastomotic approximating assembly for moving said first member and said second member relative to one another between a first, spaced position in which said tissue engaging surface is spaced from said tissue contacting surface for receiving tissue therebetween, and a second approximated position in which said tissue engaging surface and said tissue contacting surface are in close cooperative alignment; an elongated member having a proximal and distal end, said anastomotic approximating assembly being positioned at and cooperating with said distal end of said elongated member; steering means for pivoting said anastomotic approximating assembly relative to said elongated member, to thereby steer the anastomotic approximating assembly in a body cavity; and a handpiece positioned at and cooperating with said proximal end of said elongated member, said handpiece including first control means operatively connected through said elongated member with said moving means for causing said first member and said second member to move between said first and second positions; and steering control means operatively connected through said elongated member with said steering means for controlling the steering of said anastomotic approximating assembly.

According to another aspect of the invention, a steerable surgical anastomotic device is provided, comprising: anastomotic approximating assembly for approximating two ends of anastomotic tissue, for attaching portions which includes: a first member which defines a tissue engaging surface; and a second member defining a tissue contacting surface which is adapted to align with said tissue engaging surface; moving means associated with said anastomotic approximating assembly for moving said first member and said second member relative to one another between a first, spaced position in which said tissue engaging surface is spaced from said tissue contacting surface for receiving tissue therebetween, and a second approximated position in which said tissue engaging surface and said tissue contacting surface are in close cooperative alignment; imaging means associated with one of said first member and said second member for obtaining an image of an interior body region; an elongated member having a proximal and distal end, said anastomotic approximating assembly being positioned at and cooperating with said distal end of said elongated member; steering means for pivoting said anastomotic approximating assembly relative to said elongated member, to thereby steer the anastomotic approximating assembly in a body cavity; and a handpiece positioned at and cooperating with said proximal end of said elongated member, said handpiece including first control means operatively connected through said elongated member with said moving means for causing said first member and said second member to move between said first and second positions; steering control means operatively connected through said elongated member and said steering means for controlling the steering of said anastomotic approximating assembly; and viewing means operatively connected through said elongated member with said imaging means for viewing said interior body region image.

According to another aspect of the invention, an endoscopic surgical anastomotic device is provided, comprising: anastomotic approximating and attaching assembly for approximating and attaching two ends of anastomotic tissue, which includes: a first member which defines a tissue engaging surface; a second member defining a tissue contacting surface which is adapted to align with said tissue engaging surface; and tissue attaching means associated with at least one of said first member and second member for attaching the two ends of anastomotic tissue together; moving means associated with said anastomotic approximating and attaching assembly for moving said first member and said second member relative to one another between a first, spaced position in which said tissue engaging surface is spaced from said tissue contacting surface for receiving tissue therebetween, and a second approximated position in which said tissue engaging surface and said tissue contacting surface are in close cooperative alignment; imaging means associated with one of said first member and said second member for obtaining an image of an interior body region; an elongated member having a proximal and distal end, said anastomotic approximating and attaching assembly being positioned at and cooperating with said distal end of said elongated member; and a handpiece positioned at and cooperating with said proximal end of said elongated member, said handpiece including first control means operatively connected through said elongated member with said moving means for causing said first member and said second member to move between said first and second positions; second control means operatively connected through said elongated member with said second member for causing said tissue attaching means to effect attachment of the two ends of tissue to each other when the first member and second member are in the second position; and viewing means operatively connected through said elongated member with said imaging means for viewing said interior body region image.

According to another aspect of the invention a steerable surgical anastomotic device is provided, comprising: anastomotic approximating and attaching assembly for approximating and attaching two ends of anastomotic tissue, which includes: a first member which defines a tissue engaging surface; a second member defining a tissue contacting surface which is adapted to align with said tissue engaging surface; and tissue attaching means associated with at least one of said first member and second member for attaching the two ends of anastomotic tissue together; moving means associated with said anastomotic approximating and attaching assembly for moving said first member and said second member relative to one another between a first, spaced position in which said tissue engaging surface is spaced from said tissue contacting surface for receiving tissue therebetween, and a second approximated position in which said tissue engaging surface and said tissue contacting surface are in close cooperative alignment; an elongated member having a proximal and distal end, said anastomotic approximating and attaching assembly being positioned at and cooperating with said distal end of said elongated member; steering means for pivoting said anastomotic approximating and attaching assembly relative to said elongated member, to thereby steer the anastomotic approximating and attaching assembly in a body cavity; and a handpiece positioned at and cooperating with said proximal end of said elongated member, said handpiece including first control means operatively connected through said elongated member with said moving means for causing said first member and said second member to move between said first and second positions; second control means operatively connected through said elongated member with said second member for causing said tissue attaching means to effect attachment of the two ends of tissue to each other when the first member and second member are in the second position; and steering control means operatively connected through said elongated member with said steering means for controlling the steering of said anastomotic approximating and attaching assembly.

According to another object of the invention, a steerable surgical anastomotic device is provided, comprising: anastomotic approximating and attaching assembly for approximating and attaching two ends of anastomotic tissue, which includes: a first member which defines a tissue engaging surface; a second member defining a tissue contacting surface which is adapted to align with said tissue engaging surface; and tissue attaching means associated with at least one of said first member and second member for attaching the two ends of anastomotic tissue together; moving means associated with said anastomotic approximating and attaching assembly for moving said first member and said second member relative to one another between a first, spaced position in which said tissue engaging surface is spaced from said tissue contacting surface for receiving tissue therebetween, and a second approximated position in which said tissue engaging surface and said tissue contacting surface are in close cooperative alignment; imaging means associated with one of said first member and said second member for obtaining an image of an interior body region; an elongated member having a proximal and distal end, said anastomotic approximating and attaching assembly being positioned at and cooperating with said distal end of said elongated member; steering means for pivoting said anastomotic approximating and attaching assembly relative to said elongated member, to thereby steer the anastomotic approximating and attaching assembly in a body cavity; and a handpiece positioned at and cooperating with said proximal end of said elongated member, said handpiece including first control means operatively connected through said elongated member with said moving means for causing said first member and said second member to move between said first and second positions; second control means operatively connected through said elongated member with said second member for causing said tissue attaching means to effect attachment of the two ends of tissue to each other when the first member and second member are in the second position; steering control means operatively connected through said elongated member and said steering means for controlling the steering of said anastomotic approximating and attaching assembly; and viewing means operatively connected through said elongated member with said imaging means for viewing said interior body region image.

Other objects and features of the invention will become apparent from the following detailed description of a preferred embodiment of the invention, taken in conjunction with the accompanying figures.

BRIEF DESCRIPTION OF THE FIGURES

FIG. 10A is a cross-sectional view of a portion of the embodiment of FIG. 10 before either tissue portion is approximated;

FIG. 10B is a cross-sectional view of a portion of the embodiment of FIG. 10 after one tissue portion is approximated;

DETAILED DESCRIPTION OF THE PREFERRED EMBODIMENTS

Figure 1:
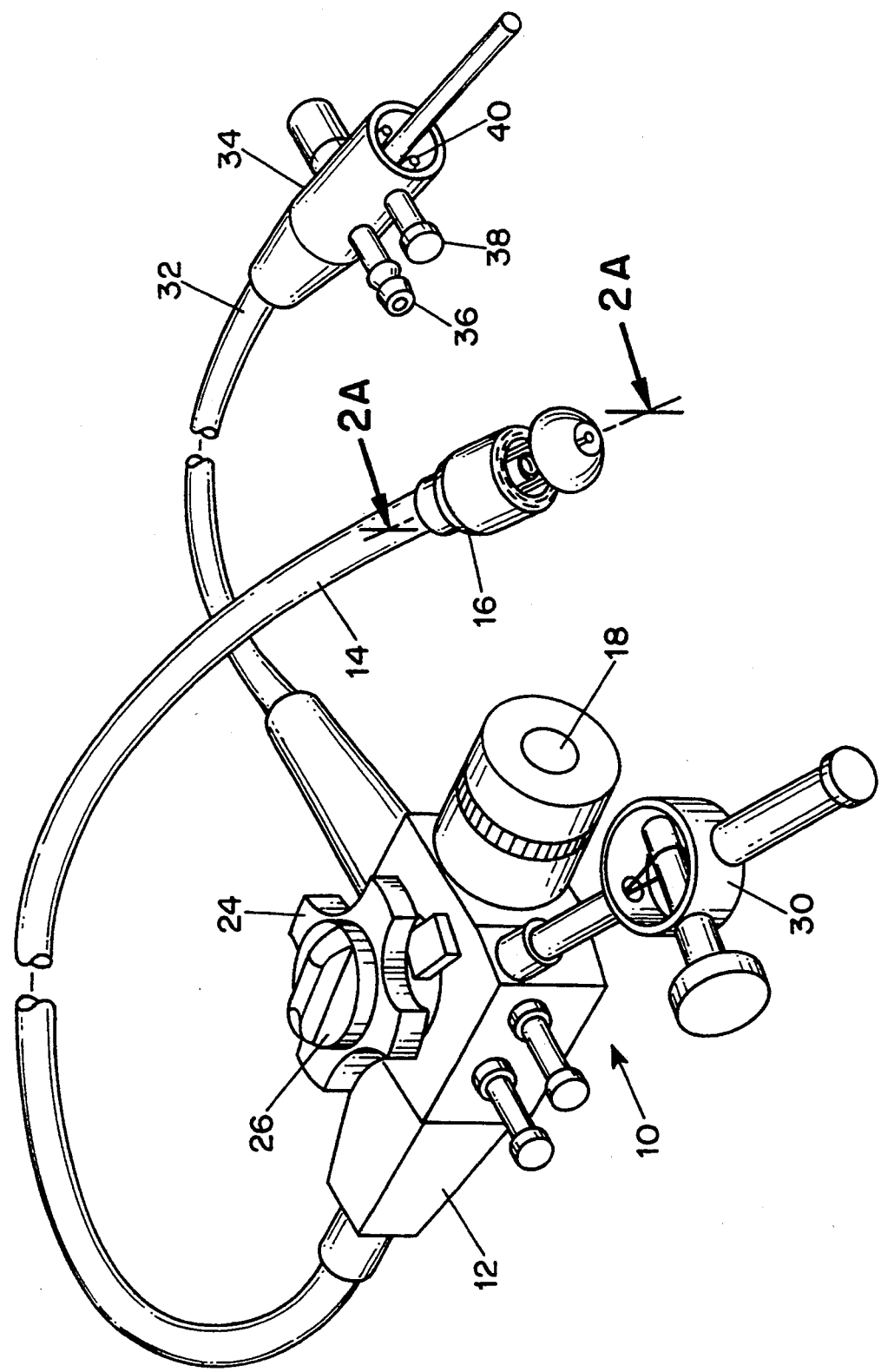
FIG. 1 is a perspective view of the stapling mechanism according to the invention, having a flexible tube, scope and steering features.

According to one aspect of the invention, an endoscopic surgical anastomotic device is provided, comprising: anastomotic approximating assembly for approximating two ends of anastomotic tissue, which includes, a first member which defines a tissue engaging surface; and a second member defining a tissue contacting, surface which is adapted to align with said tissue engaging surface; moving means associated with said anastomotic approximating assembly for moving said first member and said second member relative to one another between a first, spaced position in which said tissue engaging surface is spaced from said tissue contacting surface for receiving tissue therebetween, and a second approximated position in which said tissue engaging surface and said tissue contacting surface are in close cooperative alignment; imaging means associated with one of said first member and said second member for obtaining an image of an interior body region; an elongated member having a proximal and distal end, said anastomotic approximating assembly being positioned at and cooperating with said distal end of said elongated member; and a handpiece positioned at and cooperating with said proximal end of said elongated member, said handpiece including first control means operatively connected through said elongated member with said moving means for causing said first member and said second member to move between said first and second positions; and viewing means operatively connected through said elongated member with said imaging means for viewing said interior body region image.

According to another aspect of the invention, a steerable surgical anastomotic device is provided, comprising: anastomotic approximating assembly for approximating two ends of anastomotic tissue, for attaching operations which includes: a first member which defines a tissue engaging surface; and a second member defining a tissue contacting surface which is adapted to align with said tissue engaging surface; moving means associated with said anastomotic approximating assembly for moving said first member and said second member relative to one another between a first, spaced position in which said tissue engaging surface is spaced from said tissue contacting surface for receiving tissue therebetween, and a second approximated position in which said tissue engaging surface and said tissue contacting surface are in close cooperative alignment; an elongated member having a proximal and distal end, said anastomotic approximating assembly being positioned at and cooperating with said distal end of said elongated member; steering means for pivoting said anastomotic approximating assembly relative to said elongated member, to thereby steer the anastomotic approximating assembly in a body cavity; and a handpiece positioned at and cooperating with said proximal end of said elongated member, said handpiece including first control means operatively connected through said elongated member with said moving means for causing said first member and said second member to move between said first and second positions; and steering control means operatively connected through said elongated member with said steering means for controlling the steering of said anastomotic approximating assembly.

According to another aspect of the invention, a steerable surgical anastomotic device is provided, comprising: anastomotic approximating assembly for approximating two ends of anastomotic tissue, for attaching portions which includes: a first member which defines a tissue engaging surface; and a second member defining a tissue contacting surface which is adapted to align with said tissue engaging surface; moving means associated with said anastomotic approximating assembly for moving said first member and said second member relative to one another between a first, spaced position in which said tissue engaging surface is spaced from said tissue contacting surface for receiving tissue therebetween, and a second approximated position in which said tissue engaging surface and said tissue contacting surface are in close cooperative alignment; imaging means associated with one of said first member and said second member for obtaining an image of an interior body region; an elongated member having a proximal and distal end, said anastomotic approximating assembly being positioned at and cooperating with said distal end of said elongated member; steering means for pivoting said anastomotic approximating assembly relative to said elongated member, to thereby steer the anastomotic approximating assembly in a body cavity; and a handpiece positioned at and cooperating with said proximal end of said elongated member, said handpiece including first control means operatively connected through said elongated member with said moving means for causing said first member and said second member to move between said first and second positions; steering control means operatively connected through said elongated member and said steering means for controlling the steering of said anastomotic approximating assembly; and viewing means operatively connected through said elongated member with said imaging means for viewing said interior body region image.

According to another aspect of the invention, an endoscopic surgical anastomotic device is provided, comprising: anastomotic approximating and attaching assembly for approximating and attaching two ends of anastomotic tissue, which includes: a first member which defines a tissue engaging surface; a second member defining a tissue contacting surface which is adapted to align with said tissue engaging surface; and tissue attaching means associated with at least one of said first member and second member for attaching the two ends of anastomotic tissue together; moving means associated with said anastomotic approximating and attaching assembly for moving said first member and said second member relative to one another between a first, spaced position in which said tissue engaging surface is spaced from said tissue contacting surface for receiving tissue therebetween, and a second approximated position in which said tissue engaging surface and said tissue contacting surface are in close cooperative alignment; imaging means associated with one of said first member and said second member for obtaining an image of an interior body region; an elongated member having a proximal and distal end, said anastomotic approximating and attaching assembly being positioned at and cooperating with said distal end of said elongated member; and a handpiece positioned at and cooperating with said proximal end of said elongated member, said handpiece including first control means operatively connected through said elongated member with said moving means for causing said first member and said second member to move between said first and second positions; second control means operatively connected through said elongated member with said second member for causing said tissue attaching means to effect attachment of the two ends of tissue to each other when the first member and second member are in the second position; and viewing means operatively connected through said elongated member with said imaging means for viewing said interior body region image.

According to another aspect of the invention a steerable surgical anastomotic device is provided, comprising: anastomotic approximating and attaching assembly for approximating and attaching two ends of anastomotic tissue, which includes: a first member which defines a tissue engaging surface; a second member defining a tissue contacting surface which is adapted to align with said tissue engaging surface; and tissue attaching means associated with at least one of said first member and second member for attaching the two ends of anastomotic tissue together; moving means associated with said anastomotic approximating and attaching assembly for moving said first member and said second member relative to one another between a first, spaced position in which said tissue engaging surface is spaced from said tissue contacting surface for receiving tissue therebetween, and a second approximated position in which said tissue engaging surface and said tissue contacting surface are in close cooperative alignment; an elongated member having a proximal and distal end, said anastomotic approximating and attaching assembly being positioned at and cooperating with said distal end of said elongated member; steering means for pivoting said anastomotic approximating and attaching assembly relative to said elongated member, to thereby steer the anastomotic approximating and attaching assembly in a body cavity; and a handpiece positioned at and cooperating with said proximal end of said elongated member, said handpiece including first control means operatively connected through said elongated member with said moving means for causing said first member and said second member to move between said first and second positions; second control means operatively connected through said elongated member with said second member for causing said tissue attaching means to effect attachment of the two ends of tissue to each other when the first member and second member are in the second position; and steering control means operatively connected through said elongated member with said steering means for controlling the steering of said anastomotic approximating and attaching assembly.

According to another object of the invention, a steerable surgical anastomotic device is provided, comprising: anastomotic approximating and attaching assembly for approximating and attaching two ends of anastomotic tissue, which includes: a first member which defines a tissue engaging surface; a second member defining a tissue contacting surface which is adapted to align with said tissue engaging surface; and tissue attaching means associated with at least one of said first member and second member for attaching the two ends of anastomotic tissue together; moving means associated with said anastomotic approximating and attaching assembly for moving said first member and said second member relative to one another between a first, spaced position in which said tissue engaging surface s spaced from said tissue contacting surface for receiving tissue therebetween, and a second approximated position in which said tissue engaging surface and said tissue contacting surface are in close cooperative alignment; imaging means associated with one of said first member and said second member for obtaining an image of an interior body region; an elongated member having a proximal and distal end, said anastomotic approximating and attaching assembly being positioned at and cooperating with said distal end of said elongated member; steering means for pivoting said anastomotic approximating and attaching assembly relative to said elongated member, to thereby steer the anastomotic approximating and attaching assembly in a body cavity; and a handpiece positioned at and cooperating with said proximal end of said elongated member, said handpiece including first control means operatively connected through said elongated member with said moving means for causing said first member and said second member to move between said first and second positions; second control means operatively connected through said elongated member with said second member for causing said tissue attaching means to effect attachment of the two ends of tissue to each other when the first member and second member are in the second position; steering control means operatively connected through said elongated member and said steering means for controlling the steering of said anastomotic approximating and attaching assembly; and viewing means operatively connected through said elongated member with said imaging means for viewing said interior body region image.

The first member may comprise a first tissue clamping device and the second member may comprise a second tissue clamping device. The first clamping device may have a ratchet surfaced central shaft adapted to be received in a correspondingly arranged ratchet surfaced central opening. The moving means may comprise a cable attached at one end to the second member, and operatively attached at the other end to means for pulling the cable at the handpiece. The device may have means for cutting the cable when the first and second members are disposed in the second approximated position. The device may have means for selectively disengaging the first and second members from the elongated member. The first and second members may be made of biofragmentable material, having weakened portions which break down under bodily fluids.

The device may have means for impaling at least one tissue end and drawing it toward the other tissue end. The device may have means for impaling both tissue ends and drawing them toward each other to an approximated position.

The device may have means for injecting a tissue bonding or soldering agent to at least one of the tissue ends. The device may comprise means associated with at least one of the first and second members for applying energy to the approximated tissues to facilitate attaching of the tissues. The means for applying energy may comprise laser fiber cables. The means for applying energy may comprise an electrical coil in at least one of the first and second members.

The means for impaling may comprise at least one barb mounted on a toothed wheel, and means for rotating the toothed wheel to carry tissue impaled on the barb to an approximated position. The means for impaling may comprise at least one tissue grabber spring-biased to a retracted position, and pull means to pull the grabber to overcome the spring force to grab the tissue and pull it toward an approximated position. The means for impaling may comprise at least two grabbers operatively arranged to pivot about a common point, and pull means to pull both grabbers to pull the tissue toward an approximated position.

The device may include an electromagnet in at least one of the first and second members for generating an attraction force to pull the other of said members, when energized, to hold the tissue in an approximated position.

The means for impaling may comprise at least one barb mounted on an inflatable balloon and disposed to a first retractable position when the balloon is deflated, and to move along a path to grab the tissue by impaling it and pulling it to an approximated position as the balloon is inflated, and means for inflating the balloon.

FIG. 1 shows in perspective view, a gastrointestinal endoscopic stapler 10 according to one aspect of the present invention. A endoscopic stapler comprises a handpiece 12, a flexible tube 14 and a stapling head 16 attached to the distal end of the flexible tube. Details of the stapling head 16, including the stapling head assembly and anvil member, will be described below primarily in conjunction with other figures.

The handpiece 12 comprises scope means in the form of an eyepiece 18 which is optically coupled by means of an optical fiber or the like to a lens means 20 in the stapling head 16. The handpiece 12 also comprises steering control means in the form of two control knobs 24, 26 one of which controls the swiveling of stapling head with respect to the flexible tube 14 in a first plane, while the other knob provides for swiveling of the stapling head 16 in a second plane perpendicular to the first plane. Together the two control knobs 24, 26 provide means for positioning the stapling head at virtually any bending angle relative to the generally central axis of the flexible tube near the vicinity of the stapling head.

Figure 1A:
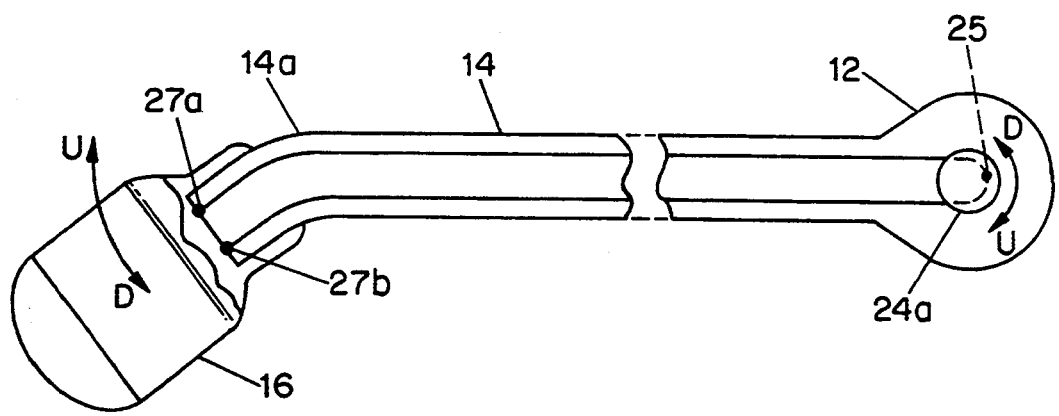
FIG. 1A is a cross-sectional view of the flexible tube, and steering mechanism.

FIG. 1A shows, in cross-section, a flexible tube 14 and steering mechanism. The flexible tube has a resilient head portion 14a, to which the stapling head 16 is attached. The resilient head 14a is more flexible then the flexible tube 14. The handpiece 12 has two pulleys, one pulley 24a being shown, which is connected to control knob 24 (not shown in FIG. 1A). Pinned to the pulley at pin point 25 is a cable 27 having one end 27a connected to the end of the resilient head portion 14a, and its other end 27b connected to the resilient head portion 14a at a diametrically opposed location to the connection of 27a. The cable 27 is channeled along its length in a suitable lumen or conduit (not shown) in flexible tube 14. By turning control knob 24 in the U(Up) or D(Down) direction, the pulley 24a will effect swivelling or bending of the resilient head portion 14a, relative to the flexible tube 14, in the U(Up) or D(Down) direction, respectively. (See also phantom lines of head assembly 50 in FIG. 2A). A similar arrangement is provided for control knob 26 for side-to-side swivelling control. Together, the two control knobs 24 and 26 provide means for positioning the stapling head 16 at virtually any desired bending angle. Further details of other bend angle positioning devices which may be used herein may be found in U.S. Pat. Nos. 4,273,111 and 4,286,585, which are incorporated by reference herein.

The handpiece also has extending from it a cable reel device 30 adapted to provide tension to and reel in, in a fishing reel like manner, a cable which extends throughout the length of the flexible tube and terminating in the distal end at the stapling head.

Also attached to the handpiece is a second flexible tube 32 which terminates at its other end in second handpiece or instrument head 34 which provides an irrigation port 36, a suction port 38, and electrical connectors 40 for connecting to a video monitor whereby the image viewable through the lens can be displayed on a video monitor, and to a power supply for energizing a light source in the stapling head. Many of the features of the scope and steering aspects of the device shown in FIG. 1, except for the stapling head 16, may be found in an instrument available from Olympus Optical Co., Ltd., as Model GIF Type XQ Scope.

Figure 2B:
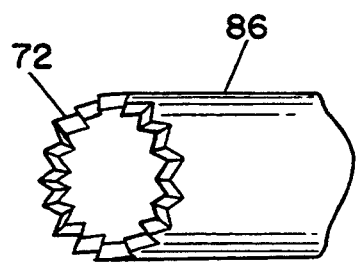
FIG. 2B is a perspective view of the alignment surface of the head mechanism of that shown in FIG. 2A.
Figure 2C:
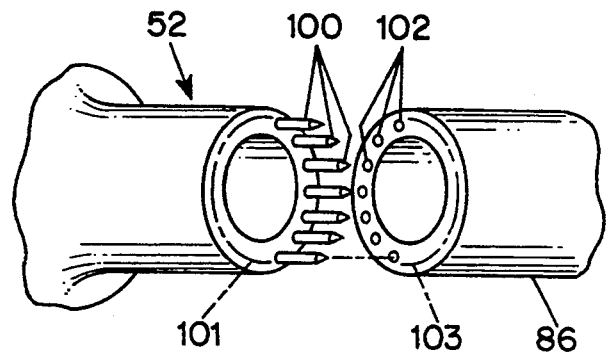
FIG. 2C is a perspective view of the different alignment arrangement from that of FIGS. 2A and 2B, for the anvil member and head mechanism.
Figure 2A:
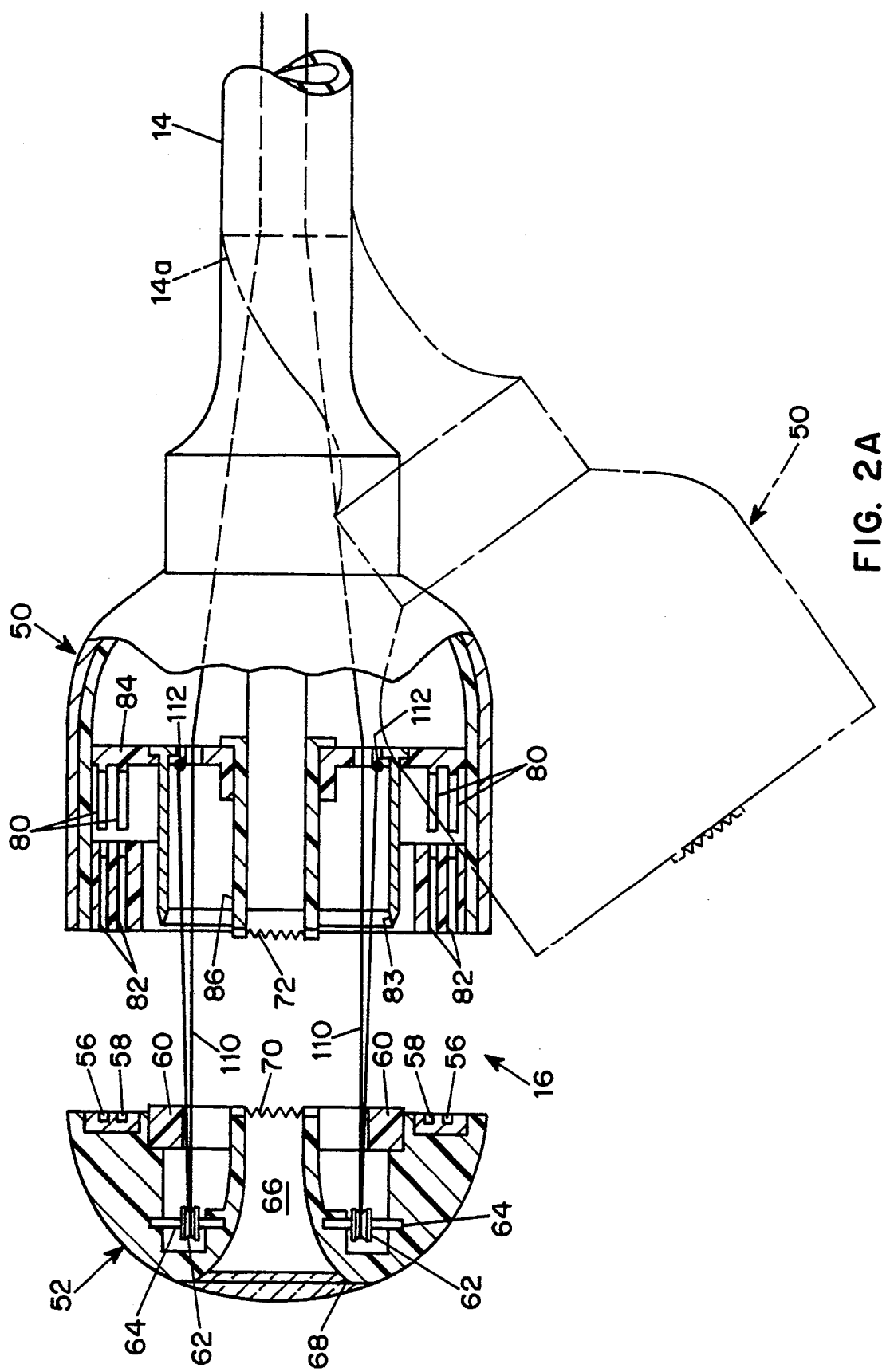
FIG. 2A is a perspective view of the stapling head mechanism and anvil, in partial cross-section, of a first embodiment according to the present invention.

Referring now to FIG. 2A, a first variation of a stapling head 16 useable in the device of FIG. 1 will now be described. The stapling head 16 comprises two major portions, a head assembly 50 connected to the distal end of a flexible tube, and an anvil member 52. The anvil member 52 has a circular anvil stapling surface 54 in the form of two concentric rings 56,58 to provide two concentric rings of equally spaced staple anvil patterns each pattern of which is similar to the anvil for a conventional paper stapler whereby a U-shaped staple driven toward the anvil will curve the two points first toward each other and then flat against the base portion of the staple to fasten material which has been pierced by the staple points. The anvil member 52 also comprises a circular or annular cutting block 60 disposed radially inwardly of the stapling anvil surface 54. The anvil member 52 also comprises two pulleys 62 arranged diametrically opposed from each other which are mounted on respective pins 64 and a central opening 66 which may have a clear window 68 of plastic or the like at the front end of the anvil member 52. The anvil member 52 also has a serrated annular 70 surface adapted to mate with a similar serrated annular surface on the head assembly 50, similar to the perimeter serrated surfaces on checkers to mate them when stacking.

The head assembly 50 has a circular staple driver assembly for driving staples in a circular array corresponding to the anvil surface, and more particularly has two rings of drivers 80 and two rings of corresponding staple holder holes 82 for driving a pattern of two annular rings of staples each ring having a equal number of equally spaced staple drivers, but with one ring rotationally offset with respect to the other ring to provide an overlapping of staples throughout the circumferential extent of the stapling pattern. This pattern of two concentric offset rings corresponds to the anvil pattern shown in part in FIG. 3. This results in a pattern of staples which minimizes or eliminates leakage of the colon after stapling. Disposed radially inwardly of the staple drivers 80 is a circular annular cutting blade 83 corresponding in size to the cutting block 60 of the anvil member 52. The staple drivers 80 and cutting blade 83 are mounted on a common mount 84 which is movable axially with respect to the exterior housing of the head assembly 50 and staple holder holes 82. As those skilled in the art will appreciate, the stapling surface 54, cutting block 60, and corresponding portions of the head assembly may be any ringed configuration other than truly circular, such as oval, elliptical, etc.

Figure 3:
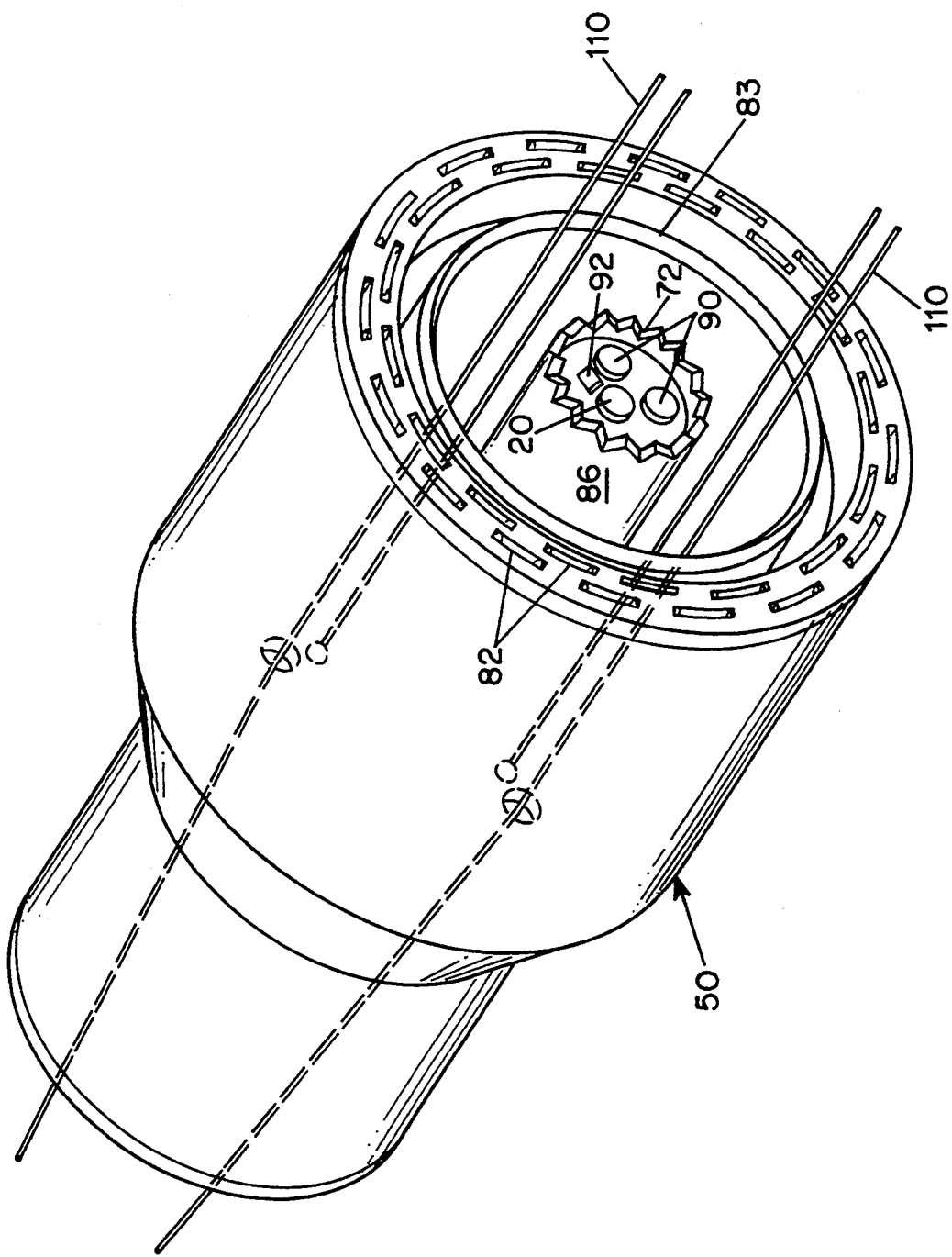
FIG. 3 is a perspective view of the stapling head mechanism of the embodiment of FIG. 2.

Disposed in the interior central portion of the head assembly 50 is a cylindrical body 85 which, as shown in more detail in FIG. 3, has two light emitting means 90, an optical lens 20, and a washing head 92. The light emitting means 90 are connected a source of light at the handpiece 12 or 34, and the lens 20 is optically connected to the eyepiece 18 of FIG. 1. The washing head 92 is connected to the irrigation port connector 36 on the second handpiece or instrument head 34 of FIG. 1, and provides a means for spraying water across the lens 20 to cleanse it.

The front surface of the cylindrical body 86 has a mating serrated surface 72 (shown in greater detail in FIG. 2B), which as described above mates with the serrated surface 70 of the anvil member 52. The serrated mating surfaces 70,72 provide a means for axially aligning the anvil member 52 with the head assembly 50. The number of serrations in each of the two serrated surfaces equals the number of anvil patterns in one of the annular rings of the staple driver assembly and anvil surface, so that when the anvil member 52 is positioned in mating arrangement with the head assembly 50, the staple drivers 80 and staple holder holes will be rotationally aligned with the anvil stapling pattern rings 56,58. The serrated surfaces 70,72 are positioned axially to provide a selected minimum distance between the anvil member 52 and head assembly 50 so as to avoid crushing of tissue located between the head assembly 50 and anvil member 52 during a stapling operation, which will be described below. The positioning of one or both of the serrated surfaces within their respective members may be adjustable, if desired, to provide means for providing an adjustable selected minimum distance between the anvil member 50 and stapling head 52.

Shown in FIG. 2C is an alternative arrangement for providing alignment of the anvil member 52 and head assembly 50. Here a circular array of pins 100 are arranged in a pattern corresponding to a circular array of funneling holes 102 in a cylindrical body 86. The pins 100 can thus pierce tissue which may be in the way of holes 102. The funneling holes 102 guide the pins 100 to mate in the holes even if initially out of rotational and/or axial alignment. The number of pins 100 and holes 102 preferably equals the number of anvil patterns and staple holes/drivers in one ring, and are rotationally positioned so that the staple holes/drivers align with the anvil patterns when the pins 100 align with the holes 102 in any rotational position. The depth of the holes 102 is longer than the pins 100 so that the surface 101 which the pins extend will be located a selected minimum distance away from surface 103 on which the holes are formed when the pins 100 are received in the holes to their full depth.

Also shown in FIG. 2A are two cables 110 each of which wraps around a different pulley 62 in the anvil member 52 and is attached at its end 112 to the common mount 84 holding the cutting blade 83 and the staple drivers 80. The two cables 110 are located on diametrically opposed sides of both the anvil member 50,52 and head assembly 50, and extend through the entire length of the flexible tube 14, terminating at the reel mechanism 30 as shown in FIG. 1. By turning the reel mechanism 30 to provide tension to the cable, the anvil member 52 will be pulled against the head assembly 50, whereby the serrated surfaces 70,72 will mate to provide axial and rotational alignment, and thereafter provide for axially moving the common mount 84 containing the cutting blade 82 and staple drivers 80 toward the anvil member 50 to effect a stapling and cutting function as will be described below. The cables 110 enter the flexible tube 14 not at the end of the sleeve 86, but at a distance from the distal end as shown in FIG. 2A.

Figure 4:
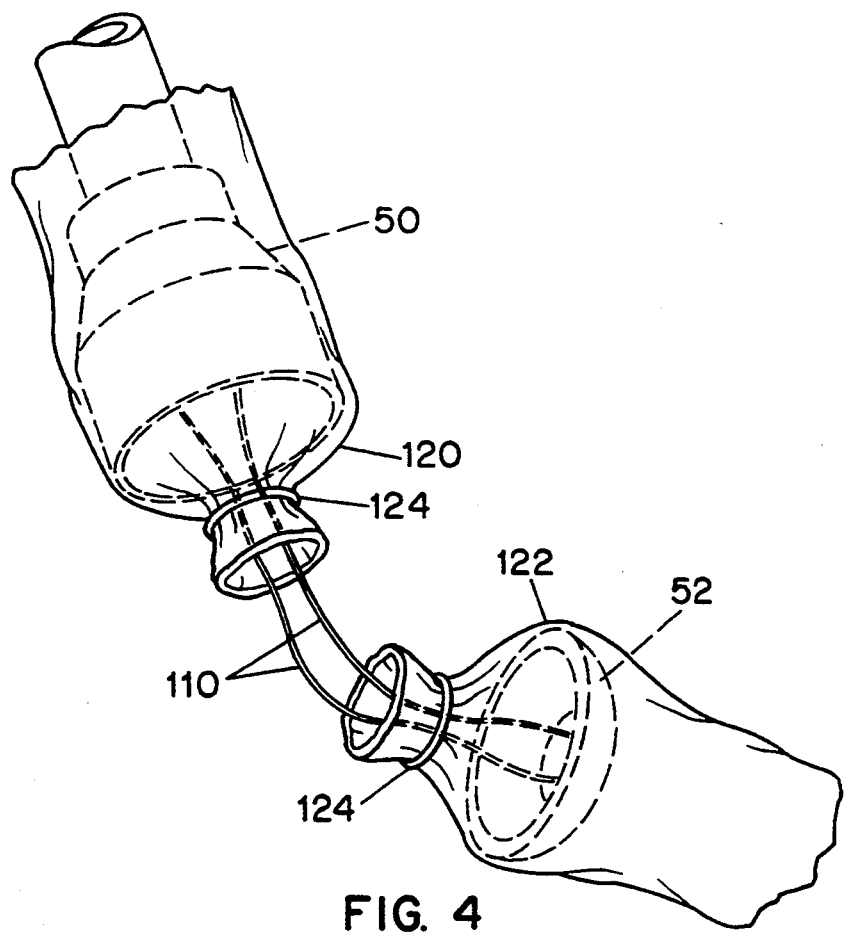
FIG. 4 is a perspective view of two ends of tubular tissue having purse string sutures, one tubular end of which encloses the anvil portion, and the other tubular section of which encloses the head mechanism, of the embodiment of FIG. 2.

Referring now to FIG. 4, two ends 120,122 of tubular colon tissue are shown, with one end 122 wrapped around the anvil member 50 and the other end wrapped around the head assembly 50. In a surgical colon resection operation for example, the distal end of the flexible tube is inserted through the rectum and by viewing through the eyepiece 18, and using other external devices known to those skilled in the art, such as ultrasound and other imaging systems, the distal end can be positioned at a desired location, such as a colon resection location. A portion of the colon which has been diseased will have been cut away using different, invasive surgical tools, leaving two unjoined sections of tubular colon 120,122.

By using the light 90 and scope (lens 20, eyepiece 18) of the present invention the head assembly 50 is positioned at the colon resection site, and using external surgical apparatus, the two ends of the colon 120,122 are tied with suture material 124 in purse-string fashion around the anvil member 52 and head assembly 50, respectively. The cables 110 which extend between the head assembly 50 and anvil member 52 are shown exposed between the two tied colon ends. Instead of string-like sutures for tying the colon ends, a flat stapling device may be used.

Figure 5:
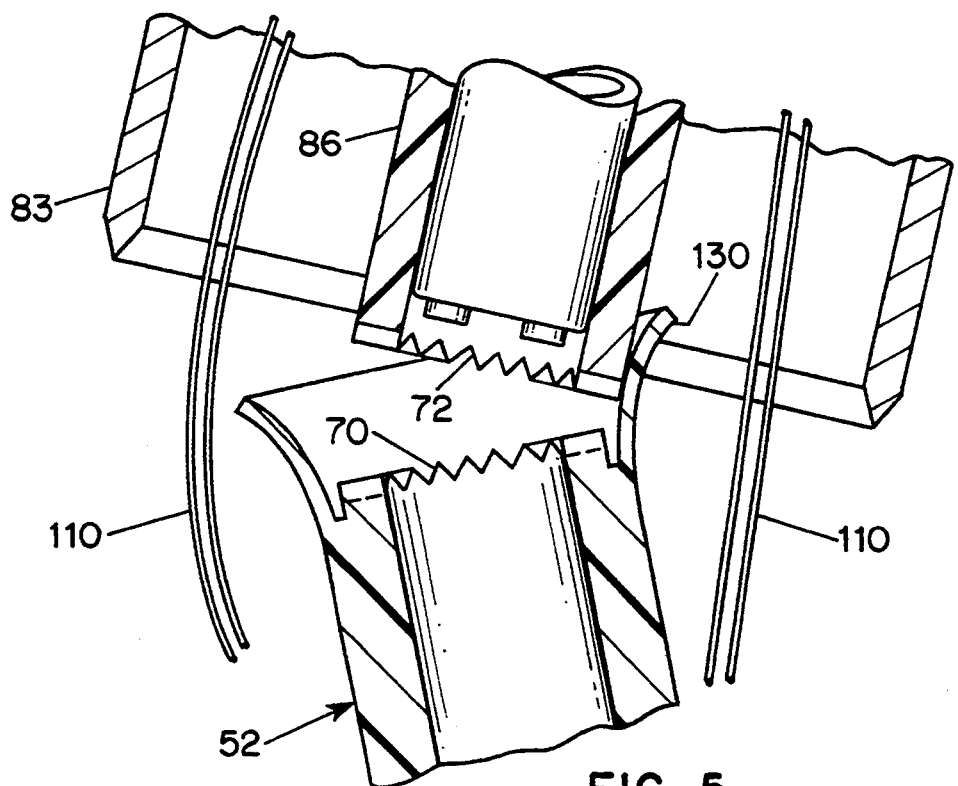
FIG. 5 is a side view in cross-section of the mating surfaces of a head mechanism and anvil of the embodiment of FIG. 2.

The reeling mechanism 30 is then operated to apply tension to the two cables 110 pulling the anvil member 52 towards the head assembly 50. It may be desired to not have the colon ends tied too tightly, so that the opening at the end of the colon even after being tied will allow the serrated mating surfaces 70,72 of the head assembly 50 and anvil member 52 to mate. The anvil member 52 may also include a outer funnelling ring 130 as shown in FIG. 5. If the alignment arrangement of FIG. 2B is used, the pins 100 can pierce any tissue getting in the way. After the anvil member 52 is pulled in contact with head assembly 50, further tensioning of the cables with the reel mechanism 30 will effect axial movement of the common mount 84 carrying the cutting blade 83 and staple drivers 80 towards the anvil member 52 to effect a stapling function and cutting away of the tubular ends of the tissue. The device may then be removed from the colon.

Figure 6:
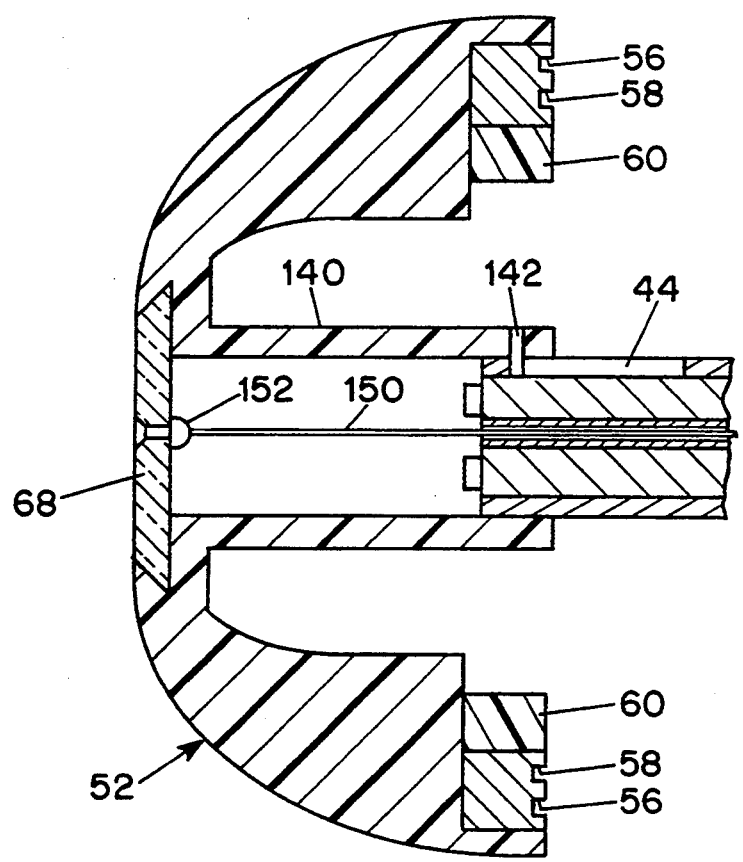
FIG. 6 is a cross-section elevational view of a head mechanism and anvil according to a second embodiment of the present invention.
Figure 7:
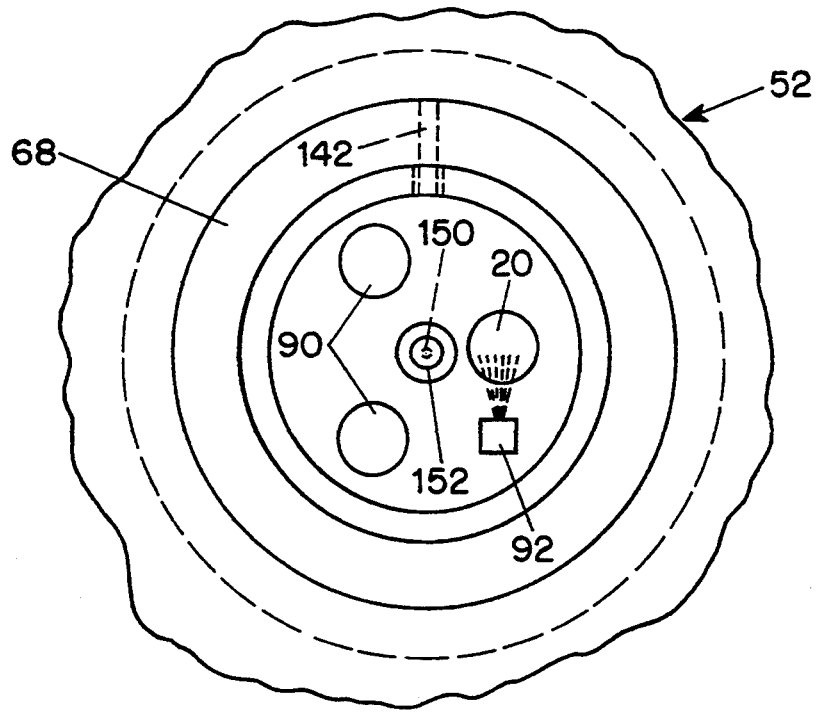
FIG. 7 is an end view of a head mechanism according to the embodiment shown in FIG. 6.

Another variation of the head assembly 50 and anvil member 52 is shown in FIGS. 6 and 7. As shown in FIG. 6, the anvil member 52 includes a cylindrical sleeve 140 having one or more guide pins 142 projecting radially inwardly, which guide pins are received in one or more corresponding slots 144 in the cylinder body 86 of the head assembly 50. This guide pin slot arrangement provides a means for axially and rotationally aligning the anvil member 52 and head assembly 50, as well as providing means for determining the minimum and maximum spacing distances between the anvil member 52 and head assembly 50.

Referring to FIG. 7, which is a front head view of the head assembly 50, a cable 150 is shown exiting a central lumen in the distal end of the flexible tube which cable 150, as shown in FIG. 6 is attached to a pin 152 centrally axially disposed on the front of the anvil member 52. While this cable 150 will be within the field of view of the region of space of the lens 20, only a slight obstruction will result. This single cable 150 performs the same function as the two cables in the first variation, namely to effect pulling of the anvil member 52 toward the head assembly 50 to a position whereby the head assembly 50 and anvil member 52 are at a selected distance close to each other but to not crush the tissue. However, in this embodiment a hydraulic means may be used for transferring force to the common mount 84, from the handpiece 12, to effect stapling by the staple driver and cutting of the tissue to remove the ends of the colon.

Figure 8:
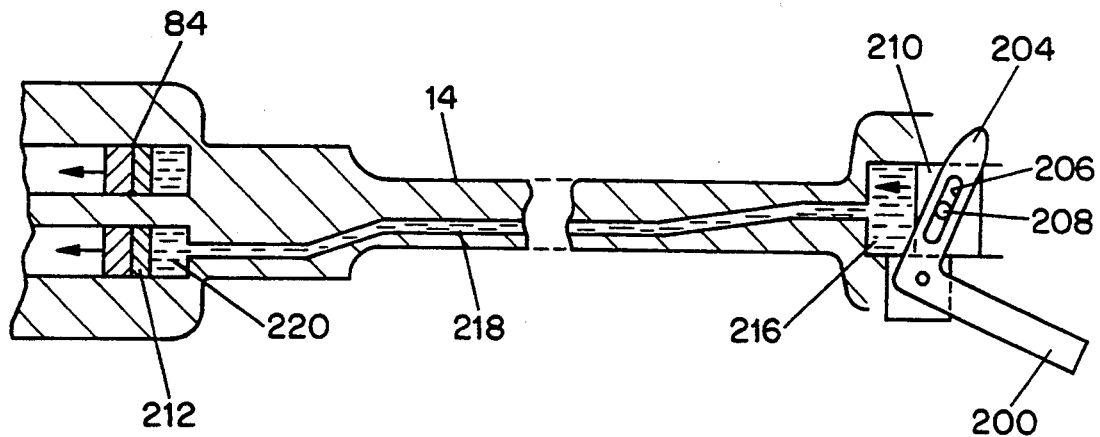
FIG. 8 is a cross-sectional view of the hydraulic actuator according to the invention, for driving staples and cutting tissue.

FIG. 8 shows an example of a hydraulic means. An actuating lever 200 located at the handpiece 12 has an L-shape and is pivotally mounted at its corner on pin 202. One of its legs 204 has an elongated slot 206 which slidingly receives pin 208 connected to a hydraulic piston 210. Piston 210 when driven to the left in FIG. 8 effects driving of piston 212 by means of hydraulic fluid 214 in cylinder 216, conduit 218 and piston 220, which piston 212 is connected to a common mount 84 to effect driving of staples and cutting of the tissue.

Other hydraulic and/or pneumatic means or the like will readily occur to those skill in the art for effecting transfer of force from the handpiece to the common mount for effecting stapling and cutting of the tissue. In particular, an arrangement may be provided for transforming relatively strong forces to the cutting head to effect stapling and cutting, but wherein the transmitted force along the flexible tube is relatively small to avoid any tendency of the flexible tube to straighten out during the stapling and cutting operation. One such design which may be used is disclosed in U.S. Pat. No. 4,485,817 which is incorporated herein by reference.

The stapling device according to the invention may be constructed for use with existing or general purpose flexible steerable scopes, or a scope may be designed particularly for use with maximizing the efficiency of the stapling mechanism. A removable stapling head and firing mechanism may be attractive to surgeons already having an existing steerable scope and already feel comfortable with its use in surgery while also lowering the cost of a stapling device.

Instead or in addition to a fiberoptic and lens at the end of the head assembly for viewing a region of space, the scope means may comprise a CCD chip at the end of the scope to provide a means for generating a two-dimensional video picture signal, using a video monitor and appropriate electronics connected to the CCD chip.

By providing a gastrointestinal stapling device having a long flexible tube (on the order of about 90 cm), virtually all colon resections could be performed through the rectum and laparoscopically, with minimal invasive surgery. In addition to colon resection, the gastrointestinal stapler could allow laparoscopic esophageal, stomach, proximal and distal small bowel and possibly biliary anastomosis to be performed. Side-to-side or end-to-side, as well as EEA could be performed with the device according to the invention.

Figure 9:
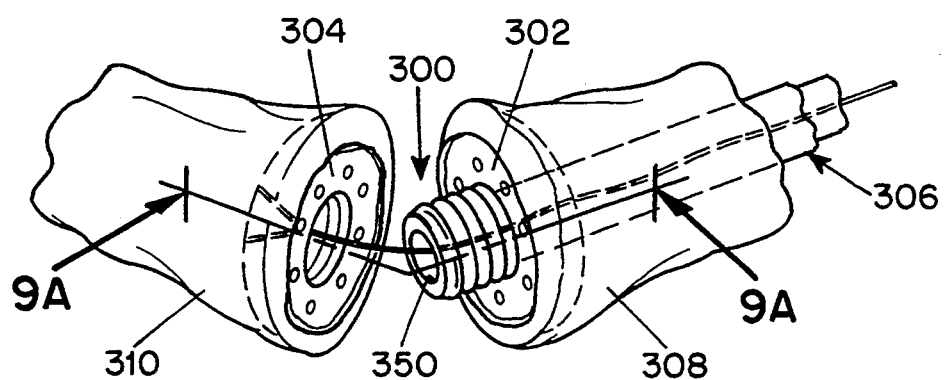
FIG. 9 is a perspective view of another embodiment for approximating and joining tissue.

The above disclosed embodiments are directed to tissue approximating devices which effect stapling of opposed ends of tubular tissue after the ends of tissue are approximated and located. Other embodiments for approximating tissue, and for effecting attachment of the tissue ends may be employed. FIG. 9 shows a perspective view of another embodiment for approximating and joining tissue. The embodiment in FIG. 9 comprises a clamping device 300. The clamping device comprises a first clamping member 302 and a second clamping member 304. The first clamping member has an actuating shaft 306, which, as will be described below, provides means for drawing the two members toward each other, and releasing the joined structure after the tissue has been approximated and clamped together.

The clamping device is inserted through a first end of tubular tissue 308 and at a first end is purse string sutured around the first clamping member 302 as shown in FIG. 9. The second clamping member 304 is adapted to receive a second tubular tissue member 310 which is likewise purse string sutured around the member.

Figure 9D:
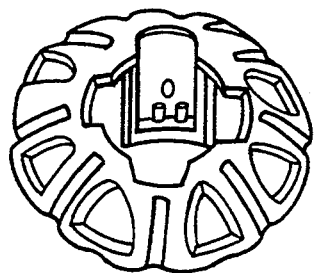
FIG. 9D is a perspective view of another clamping device which may be used in the embodiment of FIGS. 9-9C.
Figure 9A:
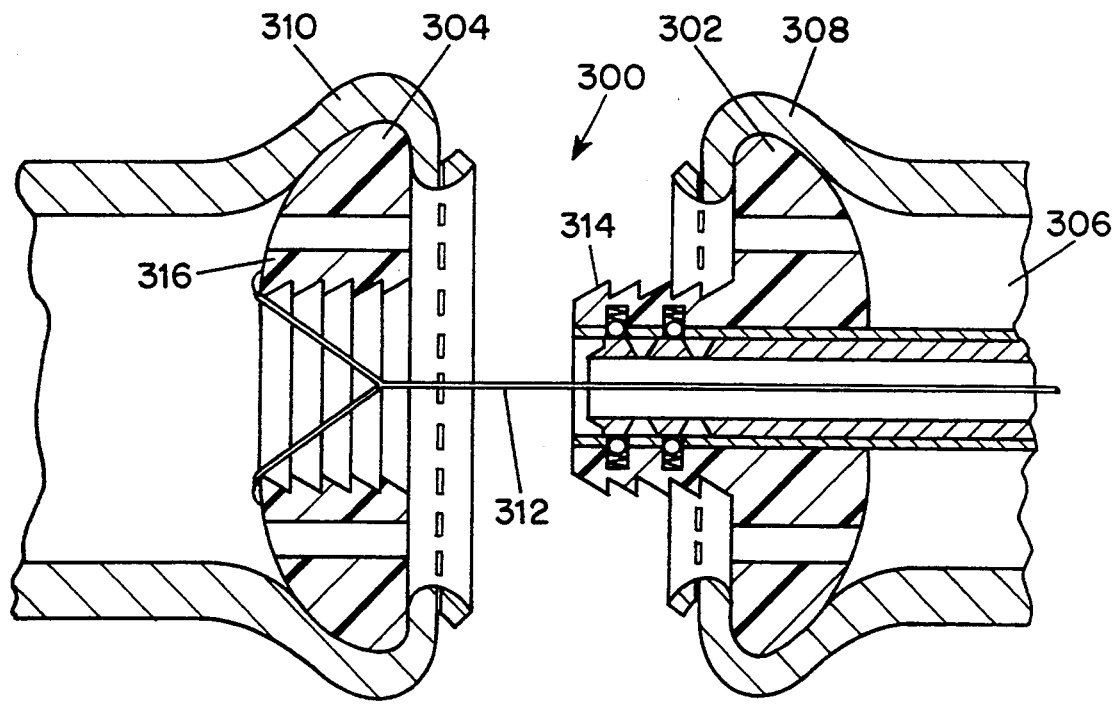
FIG. 9A is a cross-sectional view of the embodiment of FIG. 9, in the closed position, before and after respectively the cable end is cut and the central actuator is removed.
Figure 9B:
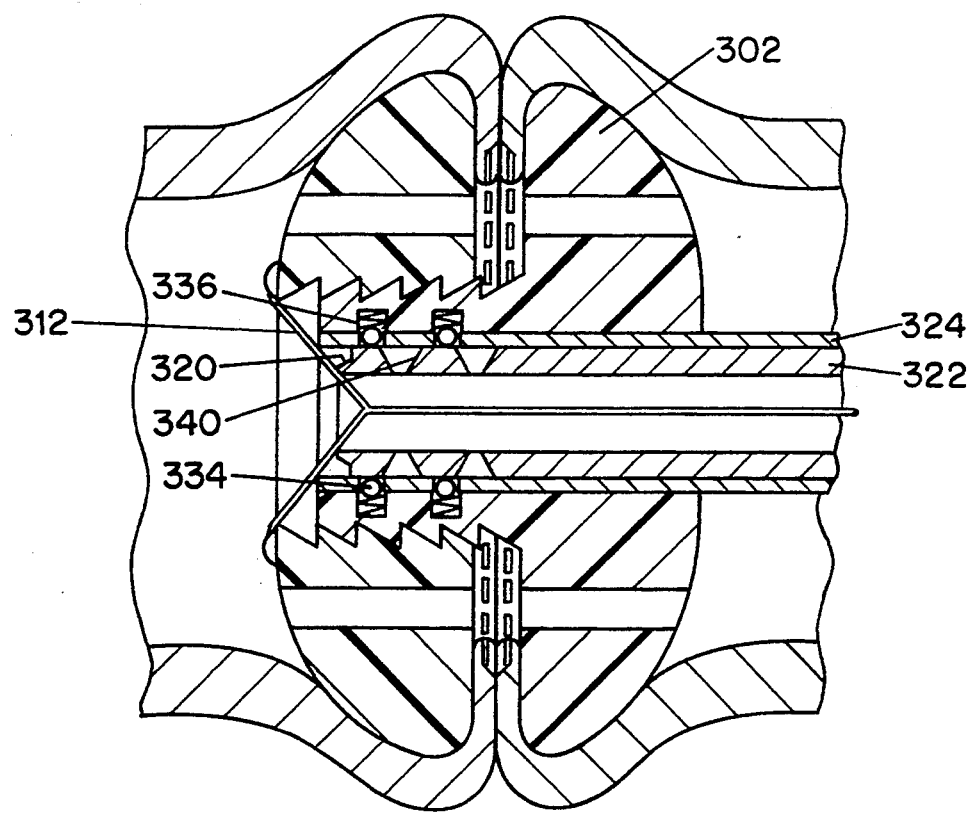
FIGS. 9B-9C are cross-sectional views of the embodiment of FIG. 9, in the closed position, before and after, respectively the cable end is cut and while the central actuator is being removed.

FIG. 9A is a cross-sectional view of the embodiment of FIG. 9, shown with the purse string sutures in place. A cable 312 which extends through a lumen in the actuating shaft 306 serves to pull the first and second members together, when the cable 312 is pulled from the right through a suitable actuating mechanism (not shown) in a handpiece or the like. The first member 302 has a ratchet surfaced central shaft 314 which is adapted to be received within a correspondingly arranged ratchet surfaced central opening 316 in the second member. By pulling the cable to the right, the first and second will be pulled toward each other and eventually assume a relationship as shown in FIG. 9B. At this point, the tissue ends are clamped together.

Figure 9C:
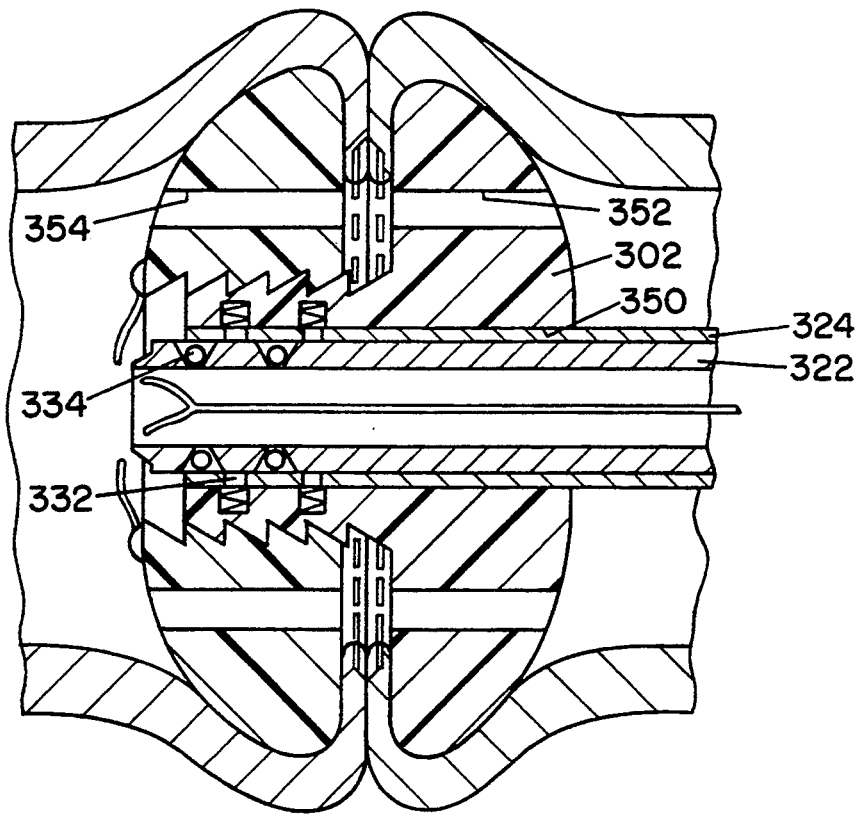

Means are provided for cutting or releasing the central cable as shown in FIG. 9C. This comprises a blade 320 on the end of an inner control shaft 320, which will cut the cable 312 when the inner control shaft 322 is pushed to the left relative to the outer control shaft 324 while the cable is held tight.

During this time, the outer control shaft 324 is held relative to the first member 302 by means of a plurality of circumferentially disposed ball and spring assemblies, four of which are shown in FIGS. 9A, 9B and 9C. For each of the ball and spring assemblies, the outer shaft 324 has an aperture 332 in its wall which receives a ball bearing 334. This ball bearing 334 is held in place by a spring 336 which serves to bias the ball 334 radially inwardly against the outer wall of inner control rod 322. The ball bearing 334 as can be seen is slightly larger in diameter than the thickness of the wall of the outer control shaft 324, so that when disposed in FIGS. 9A and 9B, the balls serve to lock outer control shaft 324 and the first member 302 in a fixed axial position relative to each other.

Means are also provided for enabling, unlocking or disengagement of the outer control shaft 324 from the first member 302. Disposed in the wall of the inner control shaft 322 are a plurality of openings 340 having a generally V-shape. When the openings 340 of the inner control shaft 322 align with the openings 324 of the outer control shaft, the springs 336 will urge the balls radially inwardly to thereby permit free axial movement between the outer control shaft 324 and first member 302. As shown in FIG. 9C, the balls are disposed in the openings 340 thereby permitting outer control shaft 324 and the inner control shaft 322 to be removed from the first member 302. The reminder of the clamping assembly, i.e. the joined first member 302 and second member 304 may be left behind, and after the crushed tissue dies the clamping device may be sloughed. The resulting clamped device, comprising the first member 302 and the second member 304, provides means for allowing the fecal matter to pass through the bowel, by means of the central axial passage 350 in the first member, and aligned passageways 352 in the first member 302 and 354 in the second member 304.

The device of FIGS. 9-9C may include clamping members similar to that shown in FIG. 9D. The device of FIG. 9D is a biofragmentable anastomosis ring which clamps the two ends of a tubular tissues together similar to the device shown in FIGS. 9–9C, but which is made of biofragmentable material which is broken by the body over time and passes out of the body after the clamping function has been completed. One such biofragmentable anastomosis ring per se is currently available under the trademark VALTRAC. FIG. 9B shows one of the two clamping members of such a VALTRAC anastomosis ring, showing a central opening a clamping device for connecting the member to a second member for clamping, and other passageways, as well as weakened portions which break down under bodily fluids over time to result in fragmenting of the device.

Figure 10:
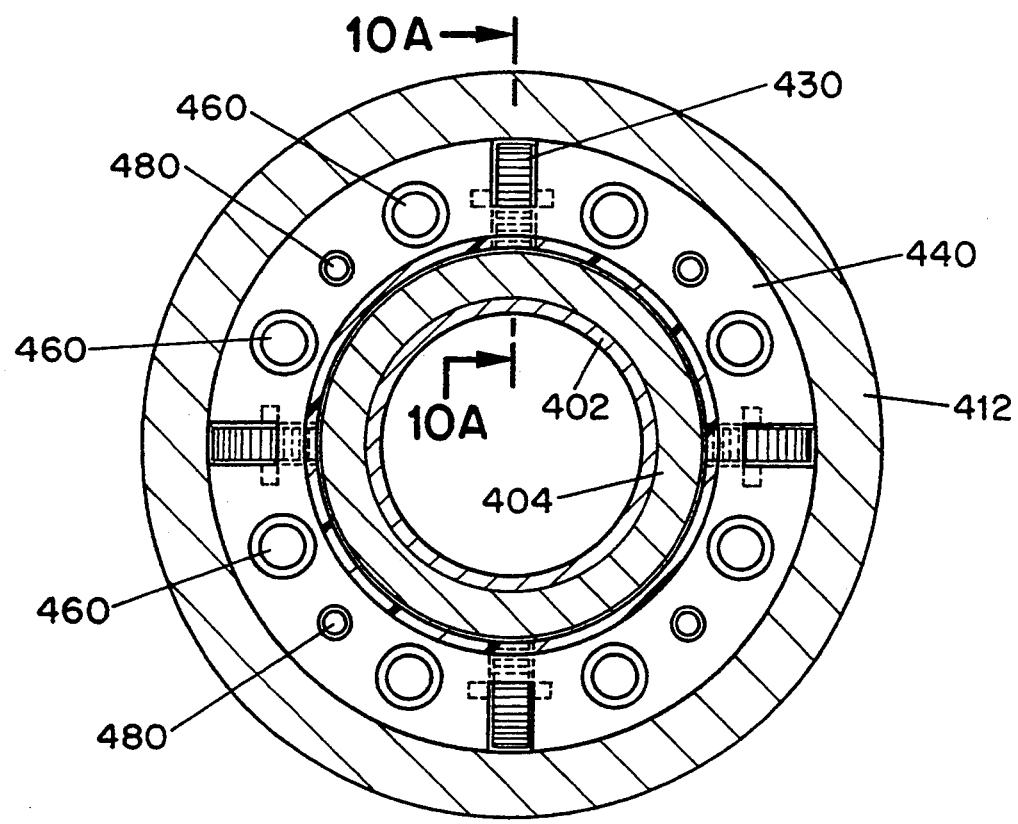
FIG. 10 is an elevational view of the face of one member of another embodiment for approximating and joining tissue, showing surgical glue parts and laser ends disposed in a ring.
Figure 10C:
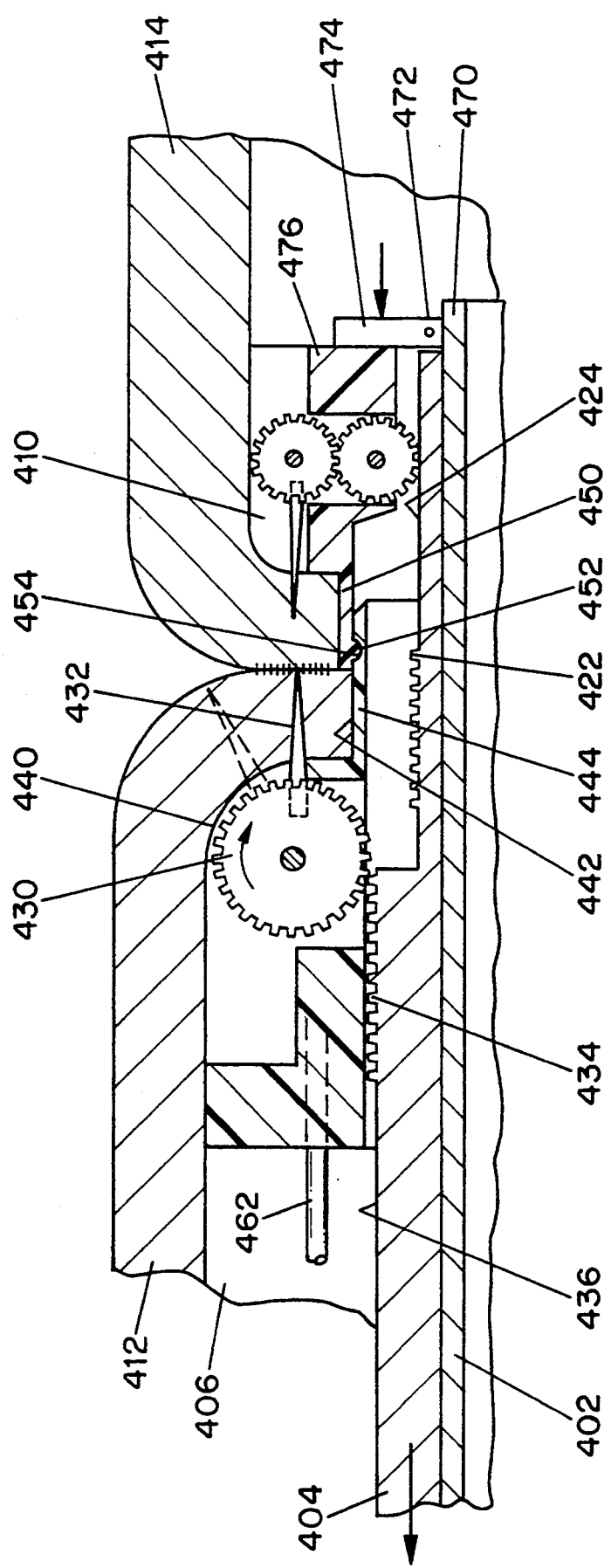
FIG. 10C is a cross-sectional view of a portion of the embodiment of FIG. 10 after both tissue portions are approximated.

FIGS. 10–10C show another embodiment for approximating and joining tissue, showing the top portion of such embodiment in cross-section. In FIG. 10A, the approximating device 400 comprises an inner control shaft 402, an outer control shaft 404, an outer housing 406 and a first tissue approximating member 408 and a second tissue approximating member 410. FIG. 10 also shows tubular tissue ends 412 and 414 which have been placed over the first member 408 and second member 410, respectively.

The second member 410 has a barb 416 mounted radially on a toothed wheel 418 meshing with toothed wheel 420, which in turn meshes with teeth 422 on a first axial surface 424 of the outer control shaft 404. The first member 408 has a toothed wheel 430 having a radially extending barb 432, which toothed wheel is adapted to mesh with teeth 434 on axial surface 436 on second central shaft 404 when the second control shaft is properly axially located relative to the toothed wheel 430, as will be explained below.

The first member 408 has a curved front portion 440 which ends in a flat axial surface 442 of front inner tube portion 444. Front inner tube portion 444 telescopes within outer tube portion 450 of the second member 410. A groove 452 in the flat axial surface 442 receives a correspondingly shaped ridge 454 radially inwardly disposed on the outer tube portion 450 of second member 410. The groove 452 and ridge 450 hold the first member 408 and second member 410 in cooperative engagement. Front inner tube portion 444 has longitudinal spacings around its radial extent so that the front portion thereof may bend radially inward. In the position shown in FIG. 10A, the teeth 434 keep the tube portion 444 in engagement with tube portion 450, so that groove 452 and ridge remain engaged and keep first member 408 and second member 410 in cooperative engagement. However, as will be discussed below in conjunction with FIGS. 10C and 10D, when the teeth 434 are axially displaced from and not below first tube portion 444, the first member 406 and second member 410 may be released from each other by pulling one member axially apart from the other member.

The outer control shaft 404 can be moved to the left relative to the first member 406 and second member 410 by moving shaft 404 at a handpiece location relative to inner control shaft 402, as shown in FIG. 10B. This results in barb 416 rotating counterclockwise and impaling the inner wall of tissue end 414 and pulling it to the left and over and down against second tube 450. A surgical glue or tissue soldering agent may be injected at port 460 through supply conduit 462 to coat the outer surface of tissue end 414.

At the position shown in FIG. 10B toothed surface 422 is out of meshing engagement with toothed wheel 420. This coincides with barb 416 ending a 180° counterclockwise rotation relative to its initial position shown in FIG. 10A. When the toothed surface 422 leaves meshing engagement with tooth wheel 420, toothed surface 434 is in meshing engagement with wheel 430, and by leftward movement of control shaft 404 to the left relative to outer housing 406, barb 432 rotates clockwise and impales tissue end 412, carrying it right and downward to abut tissue end 414 as shown in FIG. 10C.

In the position shown in FIG. 10C the tissue ends so approximated may be joined by one or more operations such as suturing, gluing, lasing, electrocauterization, or other means as will occur to those skilled in the art.

As shown in FIG. 10C, second member 410 may be urged to the right toward first member 406 to press and clamp the two tissue ends 412 and 414 together by pulling outer control shaft 404 to the left relative to outer housing 406, while keeping inner control shaft 402 inwardly to the left so that its end 470 is beyond the end 472 of outer control shaft. Pivoting stop 474 will thus be held in the vertical position as shown and will abut end 476 of second member.

Figure 10D:
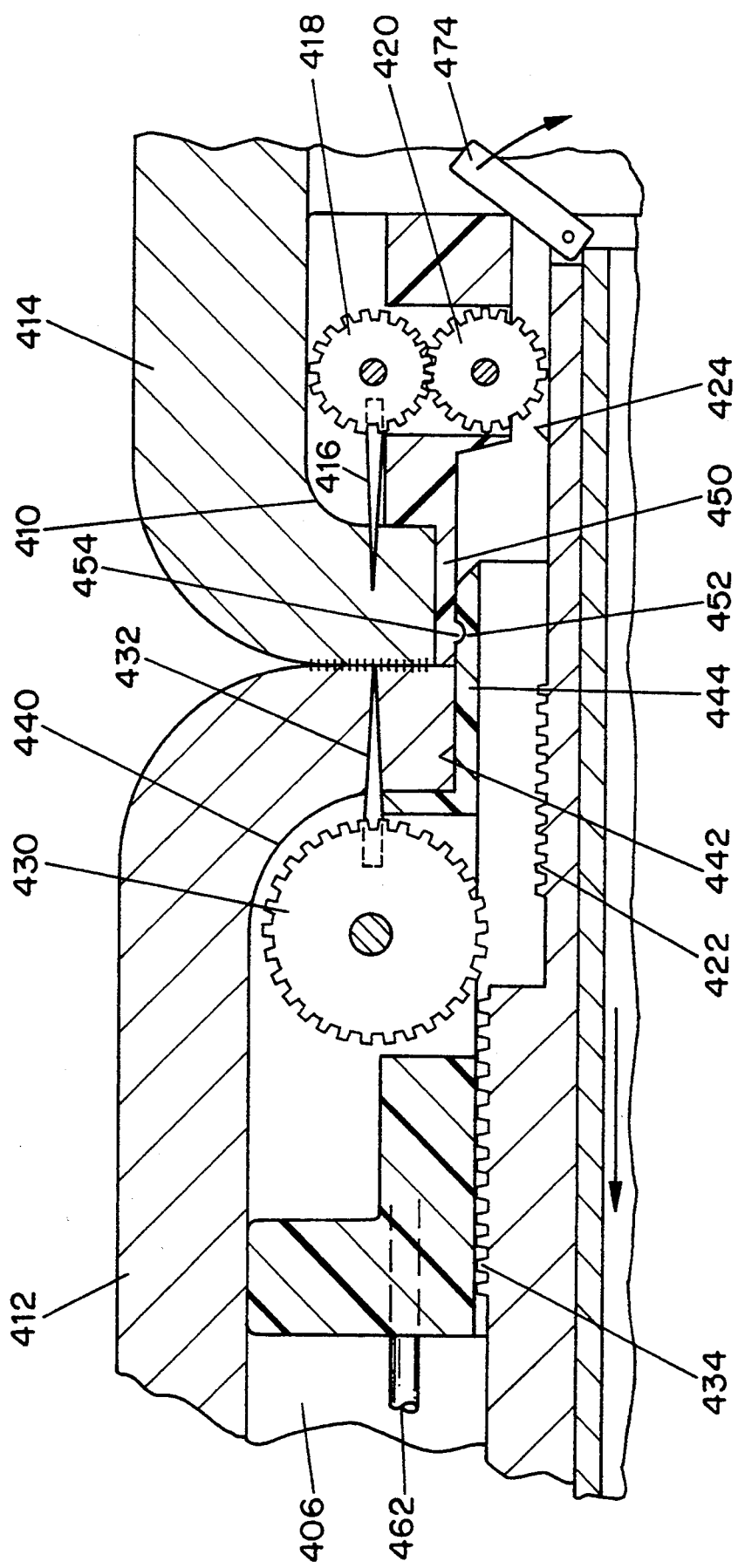
FIG. 10D is a cross-sectional view of a portion of the embodiment of FIG. 10 after both tissue portions are approximated and the central actuator being removed.

When tissue attaching operations are completed, pulling inner control shaft 402 to the left relative to outer control shaft 404 as shown in FIG. 10D will cause pivoting stop 474 to fall away, below and clearing second member 410, thereby enabling inner shaft 402, outer shaft 404, outer housing 406 and first member 406 to be withdrawn to the left from the tissue end 412. Because teeth 434 are not positioned beneath inner tube portion 444, the inner tube portion 444 may be deflect radially inwardly under the axial separation force of moving first member to left. What remains in the patient is the second member 410. Its components could be made of biofragmentable materials like the structure of FIG. 9D, to fragment and pass harmlessly out of the body. In the meantime, the center of the second member, being open, allows waste matter to pass.

While the device of FIGS. 10A–10D has been shown in partial cross-section, it should be understood that a number of these entire assemblies could be provided at different angular positions circumferentially spaced. For example, four such assemblies may be provided at 90° angular circumferential intervals as shown in FIG. 10. However, the number is not limited to four, and the number of assemblies may depend on testing, size and potential uses of the particular device.

It should be further understood that the approximating devices of FIGS. 9–9D and 10A–10D (as well as the other embodiments herein) may include steering mechanisms, scope mechanisms, stapling mechanisms and/or other types of tissue attaching mechanisms.

FIG. 10 shows a ring of ports 460 arranged circumferentially for ejecting surgical glue, a tissue soldering agent or the like. Laser fiber ends 480 are also provided for effecting lasing and welding of the tissue after the tissue ends are approximated.

Figure 11A:
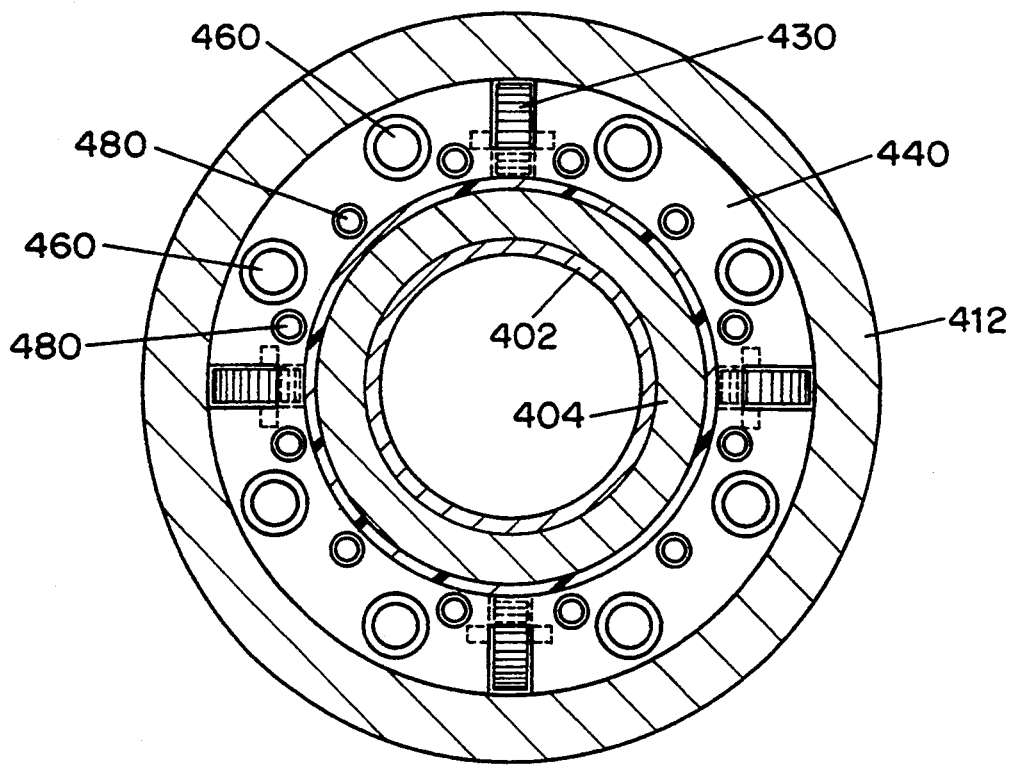
FIG. 11A is an elevational view of a modification of the embodiment of FIG. 10, showing surgical glue parts and laser ends arranged in two concentric rings.

FIG. 11A shows a similar arrangement to that of FIG. 10, except that the ports 460 are arranged in an outer ring, and the laser fiber ends 480 are arranged in an inner ring. The laser fiber ends may instead be on the outer ring.

Figure 11B:
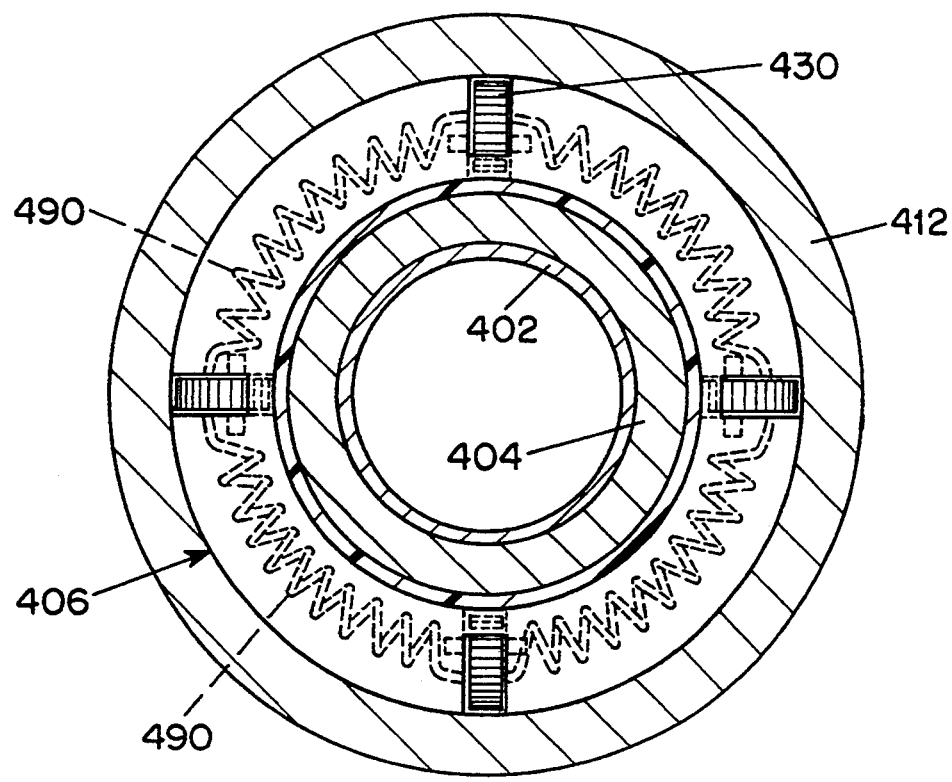
FIG. 11B is an elevational view of a modification of the embodiment of FIG. 10, showing an electromagnet in the face of tissue contact member for attracting a magnet in an opposing face of another tissue contact member.

FIG. 11b shows an alternate to or modification of the arrangement to that of FIGS. 10 and 11A, wherein face 440 of the first member 406 has an internal heater of coils 490 which effect electrocauterization of the tissue to result in bonding or attaching when electrical current is passed through the coils.

Figure 11C:
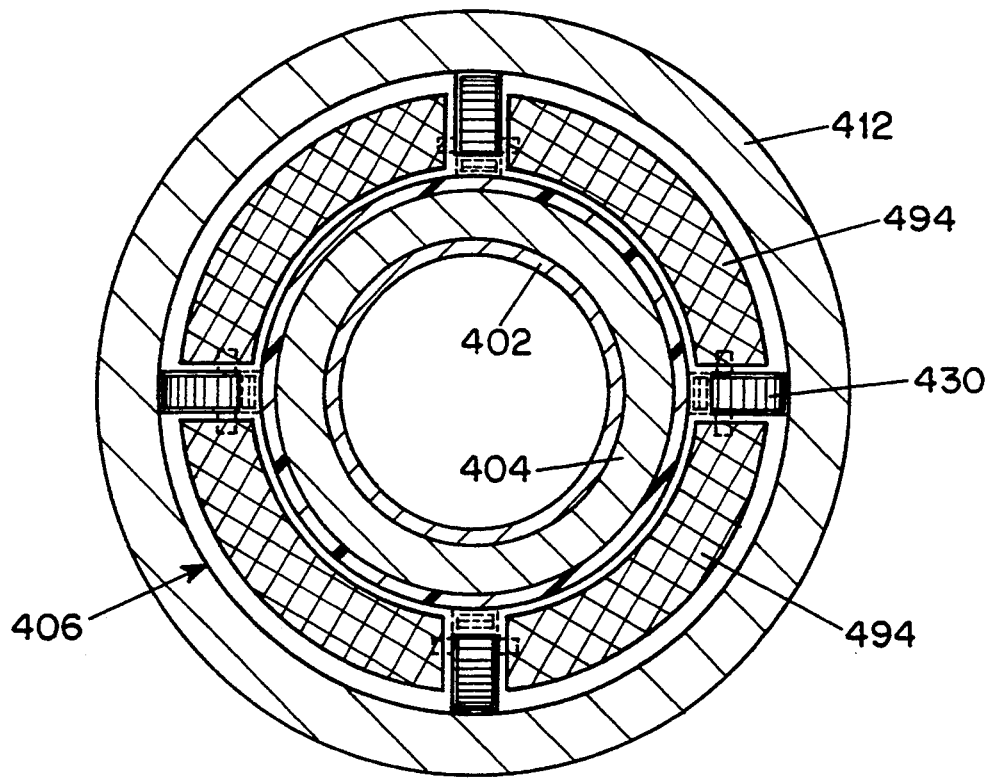
FIG. 11C is an elevational view of a modification of the embodiment of FIG. 10, showing an electrocautery device located in the face of the tissue contact member.

FIG. 11C shows another alternative or modification wherein the face 440 of the first member comprises an electromagnet 494 which when energized attracts a correspondingly shaped ring of magnetic material on the face of the second member to perform or at least assist in the tissue clamping function.

Figure 12A:
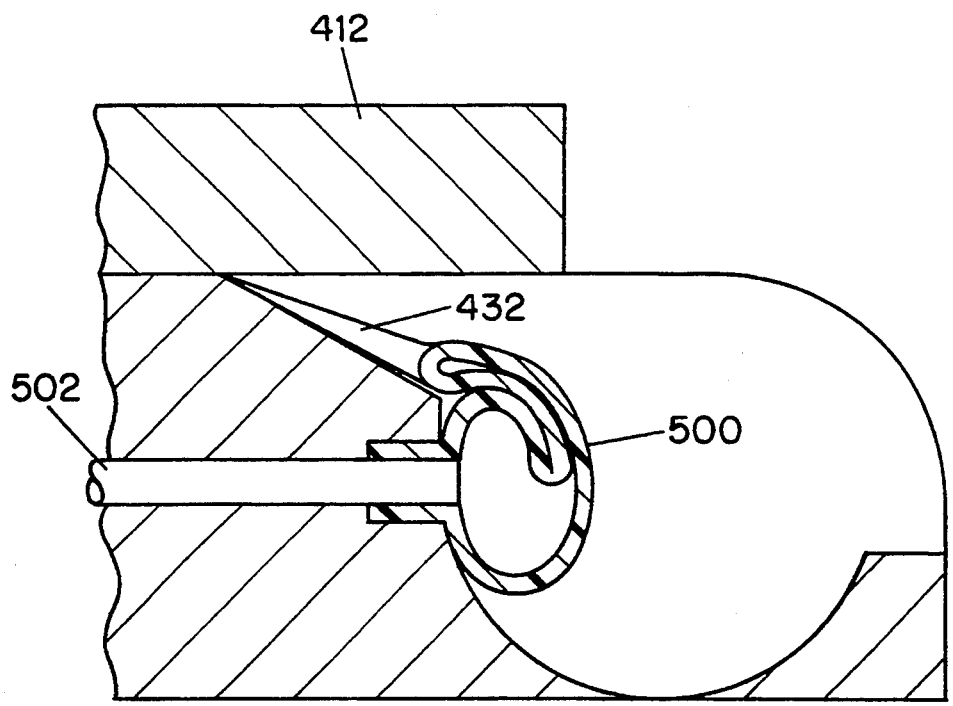
FIG. 12A is a cross-sectional view of a portion of another embodiment of a tissue approximating device before engaging one tissue portion.
Figure 12B:
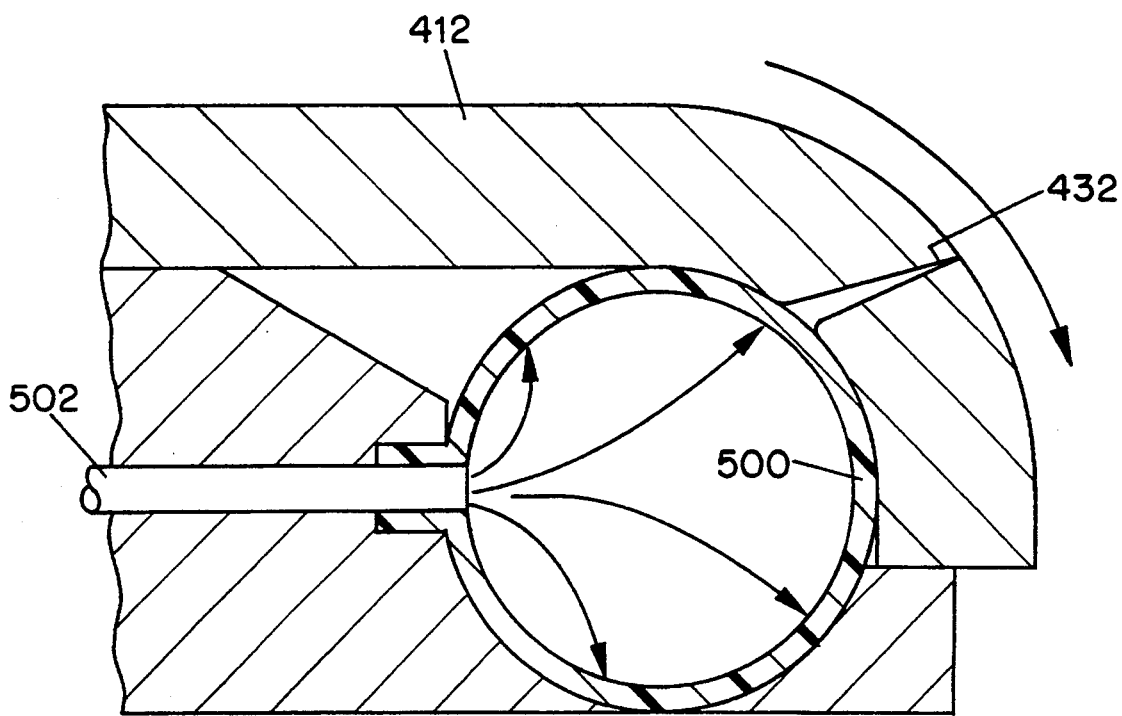
FIG. 12B is a cross-sectional view of the device of FIG. 12A engaging one tissue portion.

FIG. 12A shows an alternative to the barb arrangement of FIGS. 10A–10D. Here the barb 432 is mounted on the outside of a balloon 500 having a shape which when deflated positions the barb 432 below the tissue 412. As shown in FIG. 12B, as the balloon is inflated by supplying air or other gas through conduit 502, the barb impales the tissue and carries it to the right and downward to an approximated position similar to that of FIG. 10C.

Figure 13A:
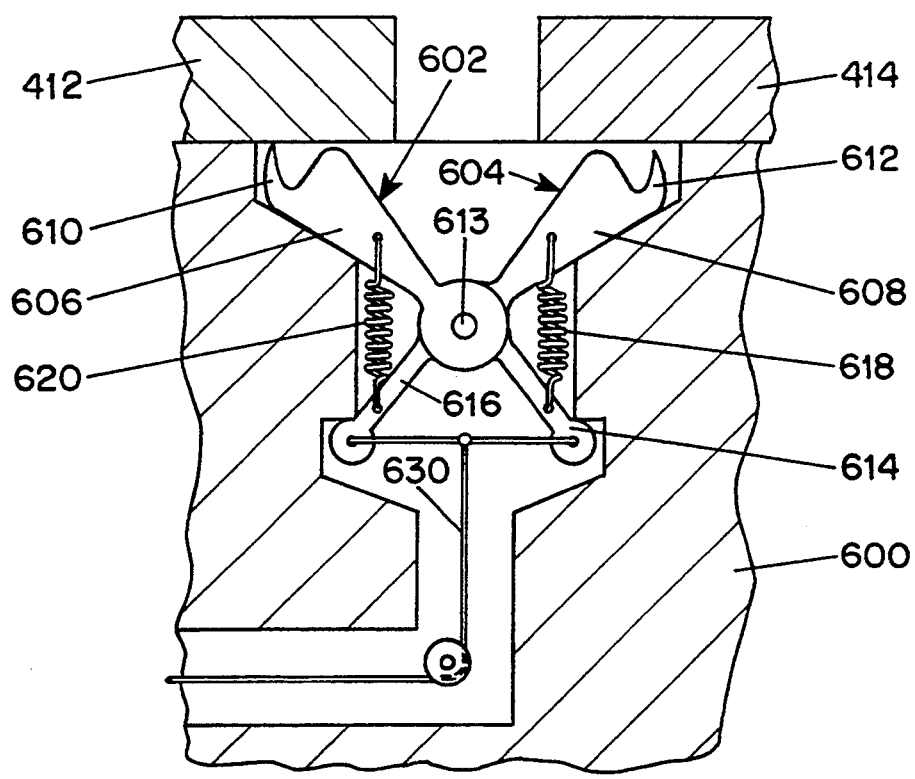
FIG. 13A is a cross-sectional view of a portion of another embodiment of a tissue approximating device before engaging two tissue portions.
Figure 13B:
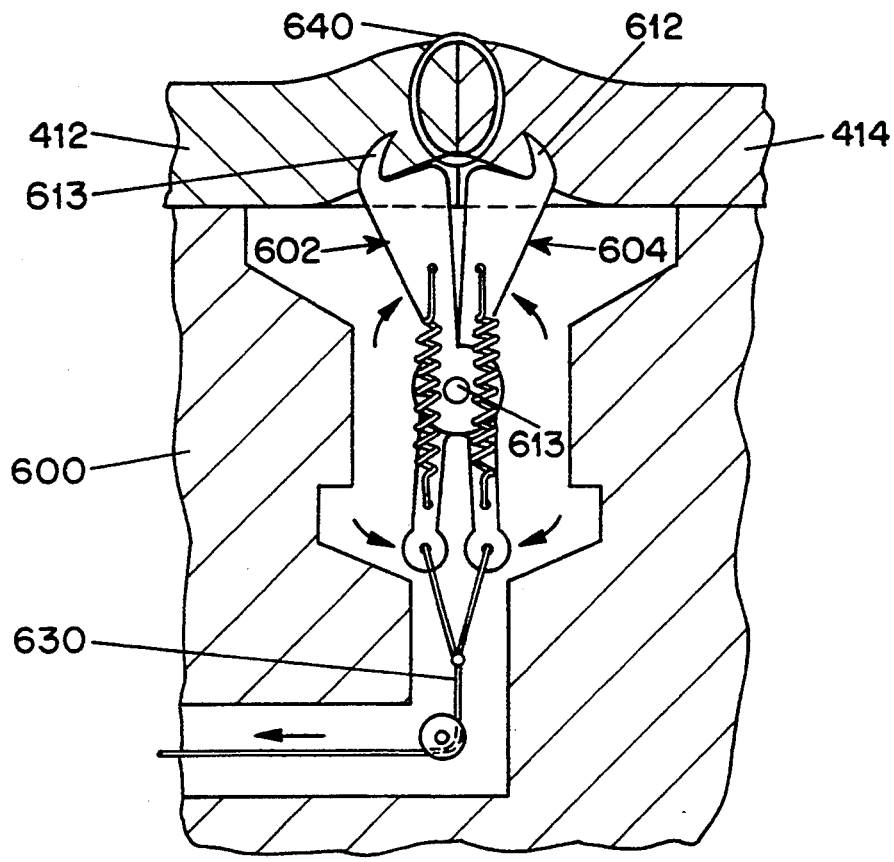
FIG. 13B is a cross-sectional view of the embodiment of 13A after the two tissue portions are approximated.

FIGS. 13A and 13B show another arrangement for approximating and holding tissue in place for tissue attaching operations. The arrangement comprises a block 600 having mounted therein a pair of tissue grabbers 602 and 604 having respective top body portions 606 and 608 and hook ends 610 and 612, commonly mounted to pivot pin 613.

The grabbers 602 and 604 have respective distal ends 614 and 616, and springs 618 and 620 connect a distal end of one grabber with the top body portion of the other grabber, biasing the hook ends 610 and 612 in the open position shown in FIG. 13A. Downward pulling on cable 630 will overcome the spring force and draw the hook ends together pulling and holding the tissue together as shown in FIG. 13B. The cable may be pulled by a suitable mechanism in a handpiece (not shown) at the end of the device. A number of such grabbing devices may be spaced circumferentially around the block, similar to the arrangement of FIGS. 10A–10D. For example, four such grabbing devices may be provided at 90° angular circumferential intervals. After the tissue ends are approximated, they are ready for attachment by one or more methods disclosed elsewhere herein, including suturing by sutures 640.

Although several embodiments of the invention with variants have been shown and described, it will readily occurred to those skilled in the art that numerous variations and modifications may be effected without departing from the true spirit and scope of the novel concept of the invention, which is limited only by way of the appended claims.

We claim:

1. An endoscopic surgical anatomotic device, comprising,
   (a) anastomotic approximating assembly for approximating two ends of anastomotic tissue, which includes:
      (i) a first member which defines a tissue engaging surface; and
      (ii) a second member defining a tissue contacting surface which is adapted to align with said tissue engaging surface;
   (b) moving means operatively connected with said anastomotic approximating assembly for moving said first member and said second member relative to one another between a first, spaced position in which said tissue engaging surface is spaced from said tissue contacting surface for receiving tissue therebetween, and a second approximated position in which said tissue engaging surface and said tissue contacting surface are in close cooperative alignment;
   (c) imaging means operatively connected with one of said first member and said second member for obtaining an image of an interior body region;
   (d) an elongated member having a proximal and distal end, said anastomotic approximating assembly being positioned at and cooperating with said distal end of said elongated member; and
   (e) a handpiece positioned at and cooperating with said proximal end of said elongated member, said handpiece including first control means operatively connected through said elongated member with said moving means for causing said first member and said second member to move between said first and second positions; and viewing means operatively connected through said elongated member with said imaging means for viewing said interior body region image.

2. The endoscopic device according to claim 1, wherein the first member comprises a first tissue clamping device and the second member comprises a second tissue clamping device, said first clamping device having a ratchet surfaced central shaft adapted to be received in a correspondingly arranged ratchet surfaced central opening.

3. The endoscopic device according to claim 1, wherein the moving means comprises a cable attached at one end to the second member, and operatively attached at the other end to means for pulling the cable at the handpiece.

4. The endoscopic device according to claim 3, further comprising means operatively connected with the cable for cutting the cable when the first and second members are disposed in the second approximated position.

5. The endoscopic device according to claim 1, further comprising means operatively connected with the first and second members for selectively disengaging the first and second members from the elongated member.

6. The endoscopic device according to claim 1, wherein the first and second members are made of biofragmentable material, having weakened portions which break down under bodily fluids.

7. The endoscopic device according to claim 1, further comprising means operatively connected with the anastomotic approximating assembly for impaling at least one tissue end and drawing it toward the other tissue end.

8. The endoscopic device according to claim 7, further comprising means operatively connected with the anastomotic approximating assembly for impaling both tissue ends and drawing them toward each other to an approximated position.

9. The endoscopic device according to claim 1, further comprising means operatively connected with the anastomotic approximating assembly for injecting a tissue bonding or soldering agent to at least one of the tissue ends.

10. The endoscopic device according to claim 1, further comprising means operatively connected with at least one of the first and second members for applying energy to the approximated tissues to facilitate attaching of the tissues.

11. The endoscopic device according to claim 10, wherein the means for applying energy comprises laser fiber cables.

12. The endoscopic device according to claim 10, wherein the means for applying energy comprises an electrical coil in at least one of the first and second members.

13. The endoscopic device according to claim 7, wherein the means for impaling comprises at least one barb mounted on a toothed wheel, and means for rotating the toothed wheel to carry tissue impaled on the barb to an approximated position.

14. The endoscopic device according to claim 7, wherein the means for impaling comprises at least one tissue grabber spring-biased to a retracted position, and a pull means to pull the grabber to overcome the spring force to grab the tissue and pull it toward an approximated position.

15. The anastomotic device according to claim 14, wherein the means for impaling comprises at least two grabbers operatively arranged to pivot about a common point, and a pull means to pull both grabbers to pull the tissue toward an approximated position.

16. The anastomotic device according to claim 7, wherein the means for impaling comprises at least one barb mounted on an inflatable balloon and disposed to a first retractable position when the balloon is deflated, and to move along a path to grab the tissue by impaling it and pulling it to an approximated position as the balloon is inflated, and means for inflating the balloon.

17. The anastomotic device according to claim 1, further comprising an electromagnet in at least one of the first and second members for generating an attraction force to pull the other of said members, when energized, to hold the tissue in an approximated position.

18. A steerable surgical anastomotic device, comprising:
   (a) anastomotic approximating assembly for approximating two ends of anastomotic tissue, for attaching operations which includes:
      (i) a first member which defines a tissue engaging surface; and
      (ii) a second member defining a tissue contacting surface which is adapted to align with said tissue engaging surface;
   (b) moving means operatively connected with said anastomotic approximating assembly for moving said first member and said second member relative to one another between a first, spaced position in which said tissue engaging surface is spaced from said tissue contacting surface for receiving tissue therebetween, and a second approximated position in which said tissue engaging surface and said tissue contacting surface are in close cooperative alignment;
   (c) an elongated member having a proximal and distal end, said anastomotic approximating assembly being positioned at and cooperating with said distal end of said elongated member;
   (d) steering means for pivoting said anastomotic approximating assembly relative to said elongated member, to thereby steer the anastomotic approximating assembly in a body cavity; and
   (e) a handpiece positioned at and cooperating with said proximal end of said elongated member, said handpiece including first control means operatively connected through said elongated member with said moving means for causing said first member and said second member to move between said first and second positions; and steering control means operatively connected through said elongated member with said steering means for controlling the steering of said anastomotic approximating assembly.

19. The anastomotic device according to claim 18, wherein the first member comprises a first tissue clamping device and the second member comprises a second tissue clamping device, said first clamping device having a ratchet surfaced central shaft adapted to be received in a correspondingly arranged ratchet surfaced central opening.

20. The anastomotic device according to claim 18, wherein the moving means comprises a cable attached at one end to the second member, and operatively attached at the other end to a means for pulling the cable at the handpiece.

21. The anastomotic device according to claim 20, further comprising means operatively connected with the cable for cutting the cable when the first and second members are disposed in the second approximated position.

22. The anastomotic device according to claim 18, further comprising means operatively connected with the anastomotic approximating assembly for selectively disengaging the first and second members from the elongated member.

23. The anastomotic device according to claim 18, wherein the first and second members are made of biofragmentable material, having weakened portions which break down under bodily fluids.

24. The endoscopic device according to claim 18, further comprising an electromagnet in at least one of the first and second members for generating an attraction force to pull the other of said members, when energized, to hold the tissue in an approximated position.

25. The endoscopic device according to claim 18, wherein the means for impaling comprises at least one barb mounted on an inflatable balloon and disposed to a first retractable position when the balloon is deflated, and to move along a path to grab the tissue by impaling it and pulling it to an approximated position as the balloon is inflated, and means for inflating the balloon.

26. The anastomotic device according to claim 18, further comprising means operatively connected with the anastomotic approximating assembly for impaling at least one tissue end and drawing it toward the other tissue end.

27. The endoscopic device according to claim 26, wherein the means for impaling comprises at least two grabbers operatively arranged to pivot about a common point, and a pull means to pull both grabbers to pull the tissue toward an approximated position.

28. The anastomotic device according to claim 26, further comprising means operatively connected with the anastomotic approximating assembly for impaling both tissue ends and drawing them toward each other to an approximate position.

29. The anastomotic device according to claim 26, wherein the means for impaling comprises at least one barb mounted on a toothed wheel, and means for rotating the toothed wheel to carry tissue impaled on the barb to an approximated position.

30. The anastomotic device according to claim 26, wherein the means for impaling comprises at least one tissue grabber spring-biased to a retracted position, and a pull means to pull the grabber to overcome the spring force to grab the tissue and pull it toward an approximated position.

31. The anastomotic device according to claim 18, further comprising means operatively connected with the anastomotic approximating assembly for injecting a tissue bonding or soldering agent to at least one of the tissue ends.

32. The anastomotic device according to claim 18, further comprising means operatively connected with at least one of the first and second members for applying energy to the approximated tissues to facilitate attaching of the tissues.

33. The anatomotic device according to claim 32, wherein the means for applying energy comprises laser fiber cables.

34. The anastomotic device according to claim 32, wherein the means for applying energy comprises an electrical coil in at least one of the first and second members.

35. A steerable surgical anastomotic device, comprising:
   (a) anastomotic approximating assembly for approximating two ends of anastomotic tissue, for attaching portions which includes:
      (i) a first member which defines a tissue engaging surface; and
      (ii) a second member defining a tissue contacting surface which is adapted to align with said tissue engaging surface;
   (b) moving means operatively connected with said anastomotic approximating assembly for moving said first member and said second member relative to one another between a first, spaced position in which said tissue engaging surface is spaced from said tissue contacting surface for receiving tissue therebetween, and a second approximated position in which said tissue engaging surface and said tissue contacting surface are in close cooperative alignment;
   (c) imaging means operatively connected with one of said first member and said second member for obtaining an image of an interior body region;
   (d) an elongated member having a proximal and distal end, said anastomotic approximating assembly being positioned at and cooperating with said distal end of said elongated member;
   (e) steering means for pivoting said anastomotic approximating assembly relative to said elongated member, to thereby steer the anastomotic approximating assembly in a body cavity; and
   (f) a handpiece positioned at and cooperating with said proximal end of said elongated member, said handpiece including first control means operatively connected through said elongated member with said moving means for causing said first member and said second member to move between said first and second positions; steering control means operatively connected through said elongated member and said steering means for controlling the steering of said anastomotic approximating assembly; and viewing means operatively connected through said elongated member with said imaging means for viewing said interior body region image.

36. An endoscopic surgical anastomotic device, comprising:
   (a) anastomotic approximating and attaching assembly for approximating and attaching two ends of anastomotic tissue, which includes:
      (i) a first member which defines a tissue engaging surface;
      (ii) a second member defining a tissue contacting surface which is adapted to align with said tissue engaging surface; and
      (iii) tissue attaching means operatively connected with at least one of said first member and second member for attaching the two ends of anastomotic tissue together;
   (b) moving means operatively connected with said anastomotic approximating and attaching assembly for moving said first member and said second member relative to one another between a first, spaced position in which said tissue engaging surface is spaced from said tissue contacting surface for receiving tissue therebetween, and a second approximated position in which said tissue engaging surface and said tissue contacting surface are in close cooperative alignment;
   (c) imaging means operatively connected with one of said first member and said second member for obtaining an image of an interior body region;
   (d) an elongated member having a proximal and distal end, said anastomotic approximating and attaching assembly being positioned at and cooperating with said distal end of said elongated member; and
   (e) a handpiece positioned at and cooperating with said proximal end of said elongated member, said handpiece including first control means operatively connected through said elongated member with said moving means for causing said first member and said second member to move between said first and second positions; second control means operatively connected through said elongated member with said second member for causing said tissue attaching means to effect attachment of the two ends of tissue to each other when the first member and second member are in the second position; and viewing means operatively connected through said elongated member with said imaging means for viewing said interior body region image.

37. A steerable surgical anastomotic device, comprising:
   (a) anastomotic approximating and attaching assembly for approximating and attaching two ends of anastomotic tissue, which includes:
      (i) a first member which defines a tissue engaging surface;
      (ii) a second member defining a tissue contacting surface which is adapted to align with said tissue engaging surface; and
      (iii) tissue attaching means operatively connected with at least one of said first member and second member for attaching the two ends of anastomotic tissue together;
   (b) moving means operatively connected with said anastomotic approximating and attaching assembly for moving said first member and said second member relative to one another between a first, spaced position in which said tissue engaging surface is spaced from said tissue contacting surface for receiving tissue therebetween, and a second approximated position in which said tissue engaging surface and said tissue contacting surface are in close cooperative alignment;
   (c) an elongated member having a proximal and distal end, said anastomotic approximating and attaching assembly being positioned at and cooperating with said distal end of said elongated member;

(d) steering means for pivoting said anastomotic approximating and attaching assembly relative to said elongated member, to thereby steer the anastomotic approximating and attaching assembly in a body cavity; and (e) a handpiece positioned at and cooperating with said proximal end of said elongated member, said handpiece including first control means operatively connected through said elongated member with said moving means for causing said first member and said second member to move between said first and second positions; second control means operatively connected through said elongated member with said second member for causing said tissue attaching means to effect attachment of the two ends of tissue to each other when the first member and second member are in the second position; and steering control means operatively connected through said elongated member with said steering means for controlling the steering of said anastomotic approximating and attaching assembly.

38. A steerable surgical anastomotic device, comprising:

(a) anastomotic approximating and attaching assembly for approximating and attaching two ends of anastomotic tissue, which includes:
   (i) a first member which defines a tissue engaging surface;
   (ii) a second member defining a tissue contacting surface which is adapted to align with said tissue engaging surface; and
   (iii) tissue attaching means operatively connected with at least one of said first member and second member for attaching the two ends of anastomotic tissue together;

(b) moving means operatively connected with said anastomotic approximating and attaching assembly for moving said first member and said second member relative to one another between a first, spaced position in which said tissue engaging surface is spaced from said tissue contacting surface for receiving tissue therebetween, and a second approximated position in which said tissue engaging surface and said tissue contacting surface are in close cooperative alignment;

(c) imaging means operatively connected with one of said first member and said second member for obtaining an image of an interior body region;

(d) an elongated member having a proximal and distal end, said anastomotic approximating and attaching assembly being positioned at and cooperating with said distal end of said elongated member;

(e) steering means for pivoting said anastomotic approximating and attaching assembly relative to said elongated member, to thereby steer the anastomotic approximating and attaching assembly in a body cavity; and (f) a handpiece positioned at and cooperating with said proximal end of said elongated member, said handpiece including first control means operatively connected through said elongated member with said moving means for causing said first member and said second member to move between said first and second positions; second control means operatively connected through said elongated member with said second member for causing said tissue attaching means to effect attachment of the two ends of tissue to each other when the first member and second member are in the second position; steering control means operatively connected through said elongated member and said steering means for controlling the steering of said anastomotic approximating and attaching assembly; and viewing means operatively connected through said elongated member with said imaging means for viewing said interior body region image.

* * * * *